(12) United States Patent
Orr et al.

(10) Patent No.: US 10,512,517 B2
(45) Date of Patent: Dec. 24, 2019

(54) MODULAR SCREW CADDY SYSTEM WITH DESCRIPTIVE LABELS

(71) Applicant: Greatbatch Ltd., Clarence, NY (US)

(72) Inventors: Kenneth Lewis Orr, Indianapolis, IN (US); Tyler P. Turk, Noblesville, IN (US)

(73) Assignee: VIANT AS&O HOLDINGS, LLC, Foxborough, MA (US)

(*) Notice: Subject to any disclaimer, the term of this patent is extended or adjusted under 35 U.S.C. 154(b) by 0 days.

(21) Appl. No.: 15/645,236

(22) Filed: Jul. 10, 2017

(65) Prior Publication Data
US 2018/0008364 A1    Jan. 11, 2018

Related U.S. Application Data

(60) Provisional application No. 62/360,035, filed on Jul. 8, 2016.

(51) Int. Cl.
*A61B 50/33* (2016.01)
*B65D 25/10* (2006.01)
(Continued)

(52) U.S. Cl.
CPC .............. *A61B 50/33* (2016.02); *A47B 81/00* (2013.01); *A61B 17/865* (2013.01); *A61B 50/20* (2016.02);
(Continued)

(58) Field of Classification Search
CPC ......... A61B 50/33; A61B 50/20; A61B 50/22; A61B 50/30; A61B 2050/0056;
(Continued)

(56) References Cited

U.S. PATENT DOCUMENTS 3,469,686 A * 9/1969 Gutsche ............ H01L 21/67346
                                                    206/518
3,718,252 A * 2/1973 Roeder ................... F16B 27/00
                                                    206/343
(Continued)

FOREIGN PATENT DOCUMENTS

DE    102007015154    9/2008
EP        1972290 A2  9/2008
(Continued)

*Primary Examiner* — Patrick D Hawn
(74) *Attorney, Agent, or Firm* — Steven J. Grossman; Grossman Tucker Perreault & Pfleger PLLC

(57) ABSTRACT

A containment case assembly, including a tray and closing lid, comprises an upper frame that is configured to support from one to a plurality of removable screw decks is described. The screw decks have a column of first openings into which removable silicon plugs or inserts are positioned. The removable inserts include indicia or labels that indicate to a user the size of a surgical screw that is positioned in a row of second openings that are aligned in the screw deck immediately adjacent to one of the first openings. The upper frame of the containment case also has an inlet provided with a series of adjacent indicia or labels that are spaced at regular millimeter intervals for use in verifying the length of a surgical screw. The upper frame is further provided with a series of regularly spaced openings that have progressively larger sizes. These openings enable a user to verify the diameter of a surgical screw.

27 Claims, 19 Drawing Sheets

(51) Int. Cl.
*B65D 43/16* (2006.01)
*B65D 25/20* (2006.01)
*B65D 25/28* (2006.01)
*B65D 43/22* (2006.01)
*A47B 81/00* (2006.01)
*A61B 50/20* (2016.01)
*A61B 50/22* (2016.01)
*A61B 50/30* (2016.01)
*A61B 17/86* (2006.01)
*A61B 50/00* (2016.01)

(52) U.S. Cl.
CPC .............. *A61B 50/22* (2016.02); *A61B 50/30* (2016.02); *B65D 25/108* (2013.01); *B65D 25/205* (2013.01); *B65D 25/282* (2013.01); *B65D 43/163* (2013.01); *B65D 43/22* (2013.01); *A61B 2050/0056* (2016.02); *A61B 2050/0067* (2016.02); *A61B 2050/0081* (2016.02); *A61B 2050/3011* (2016.02)

(58) Field of Classification Search
CPC .... A61B 2050/0067; A61B 2050/0081; A61B 2050/3011; A61B 17/865; A47B 81/00; B65D 25/108; B65D 25/205; B65D 43/163; B65D 43/22; B65D 25/282
See application file for complete search history.

(56) References Cited

U.S. PATENT DOCUMENTS

| | | | |
|---|---|---|---|
| 4,349,109 A * | 9/1982 | Scordato | B01L 9/543 206/486 |
| 4,495,150 A * | 1/1985 | Cook | B01L 9/06 134/115 R |
| 4,722,440 A | 2/1988 | Johnston et al. | |
| 4,948,442 A * | 8/1990 | Manns | B01L 3/50255 156/268 |
| 4,955,476 A | 9/1990 | Nakata et al. | |
| 5,133,939 A * | 7/1992 | Mahe | B01L 9/06 211/74 |
| 5,394,983 A * | 3/1995 | Latulippe | A61L 2/26 206/370 |
| 5,469,962 A | 11/1995 | Kitagawa et al. | |
| 5,525,314 A * | 6/1996 | Hurson | A61C 3/04 206/369 |
| 5,579,929 A | 12/1996 | Schwartz | |
| 5,732,821 A * | 3/1998 | Stone | A61L 2/26 206/370 |
| 5,996,818 A * | 12/1999 | Boje | B01L 9/06 206/443 |
| 6,012,577 A * | 1/2000 | Lewis | A61L 2/26 206/370 |
| 6,019,225 A | 2/2000 | Kalmakis et al. | |
| 6,132,684 A * | 10/2000 | Marino | B01L 9/06 211/74 |
| 6,286,678 B1 | 9/2001 | Petrek | |
| 6,474,481 B1 | 11/2002 | Liu | |
| 6,533,133 B2 * | 3/2003 | Liu | B01L 9/06 211/74 |
| 6,568,544 B1 * | 5/2003 | Lafond | B01L 9/06 211/74 |
| 6,991,108 B1 * | 1/2006 | Rorato | A61L 2/26 206/503 |
| D557,814 S * | 12/2007 | Glenn | D24/217 |
| 7,350,643 B2 | 4/2008 | Knopfle et al. | |
| 7,650,991 B2 | 1/2010 | Hester et al. | |
| 8,061,517 B2 | 11/2011 | Loeffler et al. | |
| 8,079,468 B2 * | 12/2011 | Pleil | A61B 90/04 206/339 |
| 8,079,518 B2 * | 12/2011 | Turner | G09F 3/0292 235/375 |
| 8,490,790 B2 | 7/2013 | Cocheteux et al. | |
| 8,556,074 B2 * | 10/2013 | Turner | A61F 2/0095 206/339 |
| 8,685,068 B2 | 4/2014 | Francese et al. | |
| 8,821,556 B2 | 9/2014 | Brand et al. | |
| 8,911,233 B2 | 12/2014 | Moore | |
| 9,107,502 B2 | 8/2015 | Schindler et al. | |
| 9,757,171 B2 * | 9/2017 | Sixto | A61B 17/8014 |
| 2002/0153336 A1 * | 10/2002 | Wang | A47F 7/0028 211/60.1 |
| 2007/0095689 A1 * | 5/2007 | Pratt | A61B 50/30 206/366 |
| 2008/0190932 A1 * | 8/2008 | Orr | B65D 7/06 220/318 |
| 2008/0230423 A1 | 9/2008 | Loeffler et al. | |
| 2010/0069969 A1 | 3/2010 | Ampuero et al. | |
| 2011/0071572 A1 * | 3/2011 | Sixto | A61B 17/8014 606/286 |
| 2011/0108446 A1 | 5/2011 | Bettenhausen et al. | |
| 2011/0288596 A1 | 11/2011 | Brand et al. | |
| 2016/0194114 A1 * | 7/2016 | Luna | B65D 25/34 220/732 |

FOREIGN PATENT DOCUMENTS

| | | |
|---|---|---|
| EP | 1972290 A3 | 6/2009 |
| WO | 2006136291 | 12/2006 |
| WO | 2010030845 | 3/2010 |
| WO | 2010097447 A2 | 9/2010 |
| WO | 2010097447 A3 | 9/2010 |

* cited by examiner

MODULAR SCREW CADDY SYSTEM WITH DESCRIPTIVE LABELS

CROSS-REFERENCE TO RELATED APPLICATION

This application claims priority to U.S. provisional patent application Ser. No. 62/360,035, filed on Jul. 8, 2016.

BACKGROUND OF THE INVENTION

1. Field of the Invention

The present invention generally relates to the field of orthopedic containment tray assemblies and, in particular, containment tray assemblies that are configured for use with a wide variety of orthopedic surgical fasteners, for example orthopedic surgical screws. More particularly, the present invention relates to a system for holding and organizing surgical screws.

2. Prior Art

Surgical screws must be cleaned and sterilized before they can be used for surgery. For this purpose, the surgical screws are preferably stored in a tray. Before use in surgery, the tray holding the screws is placed in a cleaning or sterilization chamber into which a cleaning fluid or sterilization medium (such as hot water vapor or ethylene oxide) is introduced. To obtain a good cleaning or sterilization result, the surgical screws are preferably arranged in the tray such that the sterilization medium can fully access the screws. It is also preferable that the screws can be easily removed from the tray after the cleaning or sterilization operation for subsequent use in a surgical procedure.

SUMMARY OF THE INVENTION

The present invention relates to a containment case assembly, including a tray and closing lid, comprises an upper frame that is configured to support from one to a plurality of removable screw decks. The screw decks have a column of first openings into which removable silicon plugs or inserts are positioned. The removable inserts include indicia or labels that indicate to a user the size of a surgical screw that is positioned in a row of second openings that are aligned in the screw deck immediately adjacent to one of the first openings. The upper frame of the containment case also has an inlet provided with a series of adjacent indicia or labels that are spaced at regular millimeter intervals for use in verifying the length of a surgical screw. The upper frame is further provided with a series of regularly spaced openings that have progressively larger sizes. These openings enable a user to verify the diameter of a surgical screw.

Thus, one object of the present disclosure is to describe a containment tray for holding and organizing surgical screws. The tray comprises: a base plate having a rectangular shape; a main frame having a rectangular shape and comprising spaced-apart upper and lower main frame sides extending to and meeting with right and left main frame edges; a first support, a second support, a third support, and a fourth support, each corner support extending from and connected to the base plate and the main frame; a least one screw deck, comprising: a substantially planar upper deck plate extending along a longitudinal axis to spaced-apart right and left upper plate sides meeting opposed first and second upper plate ends, wherein the upper deck plate has a plurality of spaced apart first openings and a plurality of spaced apart second openings; a lower deck plate comprising spaced-apart right and left lower plate sides meeting opposed first and second lower plate ends, the lower deck plate comprising a substantially planar central lower plate portion meeting upwardly extending webs joined to first and second planar lower plate lips to thereby provide an elongated U-shape in cross-section extending along the longitudinal axis, wherein the first and second lower plate lips are secured to the upper deck plate ends so that the central lower plate portion is spaced from the upper deck plate, and wherein the lower deck plate has a plurality of spaced apart third openings, the second openings in the upper deck plate being aligned directly above the third openings in the lower deck plate; at least one screw that is sized to be removably received in the plurality of second openings; and at least one insert that is sized to removably fit into the plurality of first openings in the upper deck plate, wherein the insert is provided with a first label that correlates to a first characteristic of the at least one screw.

Another object of the present invention is to provide a screw deck for holding a screw, the screw deck comprising: a substantially planar upper deck plate extending along a longitudinal axis to spaced-apart right and left upper plate sides meeting opposed first and second upper plate ends, wherein the upper deck plate has a plurality of spaced apart first openings and a plurality of spaced apart second openings; and a lower deck plate comprising spaced-apart right and left lower plate sides meeting opposed first and second lower plate ends, the lower deck plate comprising a substantially planar central lower plate portion meeting upwardly extending webs joined to first and second planar lower plate lips to thereby provide an elongated U-shape in cross-section extending along the longitudinal axis, wherein the first and second lower plate lips are secured to the upper deck plate ends so that the central lower plate portion is spaced from the upper deck plate, and wherein the lower deck plate has a plurality of spaced apart third openings, wherein the second openings in the upper deck plate are aligned directly above the third openings in the lower deck plate. Continuing, the first openings in the upper deck plate are arranged in a first column extending parallel to the longitudinal axis and adjacent to one of the right and left upper plate sides; and the second openings in the upper deck plate are arranged in a second column extending parallel to the longitudinal axis, the first and second openings in the upper deck plate being aligned one immediately adjacent to the other; and the third openings in the lower deck plate are arranged in a third column aligned directly below the second openings in the second column.

Moreover, another object of the present invention is to provide a system for holding and organizing at least two screws, the system comprising: a screw deck, comprising: a substantially planar upper deck plate extending along a longitudinal axis to spaced-apart right and left upper plate sides meeting opposed first and second upper plate ends, wherein the upper deck plate has a plurality of spaced apart first openings and a plurality of spaced apart second openings; a lower deck plate comprising spaced-apart right and left lower plate sides meeting opposed first and second lower plate ends, the lower deck plate comprising a substantially planar central lower plate portion meeting upwardly extending webs joined to first and second planar lower plate lips to thereby provide an elongated U-shape in cross-section extending along the longitudinal axis, wherein the first and second lower plate lips are secured to the upper deck plate ends so that the central lower plate portion is spaced from the upper deck plate, and wherein the lower deck plate has a plurality of spaced apart third openings, the second openings in the upper deck plate being aligned directly above the third openings in the lower deck plate; at least one screw that is sized to be removably received in the plurality of second openings in the upper deck plate; and at least one insert that is sized to removably fit into the plurality of first openings in the upper deck plate, wherein the insert is provided with a first label that correlates to a first characteristic of the at least one screw. The first openings in the upper deck plate are arranged in a first column extending parallel to the longitudinal axis and adjacent to one of the right and left upper plate sides; and the second openings in the upper deck plate are arranged in a second column extending parallel to the longitudinal axis, the first and second openings in the upper deck plate being aligned one immediately adjacent to the other; and the third openings in the lower deck plate are arranged in a third column aligned directly below the second openings in the second column. The plurality of second and third openings in the respective upper and lower deck plates are arranged in at least two columns, each column having from 2 to 30 openings. The plurality of second and third openings in the respective upper and lower deck plates are arranged in from two to seven columns, each column having from 2 to 30 openings. The first and second openings in the upper deck plate are of the same or different size. The first label on the removable insert correlates to a length of the at least one screw. The opposed first and second upper plate ends are provided with respective inlets that are spaced inwardly from the right and left upper plate sides. The inlet plates are sized to fit into the inlets in the opposed first and second upper plate ends. The inlet plates are provided with a second label corresponding to a second characteristic of the at least one screw. The second label on the inlet plates correlates to at least one of a diameter and a type of the at least one screw. The opposed first and second lower plate lips at the opposed first and second lower plate ends are provided with lip openings that are aligned with the respective inlets in the opposed first and second upper plate ends.

In one embodiment there is a plurality of inserts, each insert being sized to removably fit into one of the plurality of first openings in the upper deck plate, and wherein at least two of the inserts have a different first label.

In one embodiment there is a plurality of screws, each screw being sized to be removably received in one of the plurality of second openings in the upper deck plate. At least one of the screws is sized to be removably received in one of the plurality of aligned second and third openings in the respective upper deck plate and the lower deck plate.

Related objects and advantages of the present invention will be apparent from the following detailed description and the appended drawings.

The present invention will now be described in connection with preferred embodiments, however, it is understood that there is no intent to limit the invention to the embodiments described. On the contrary, the intent is to cover all alternatives, modifications, and equivalents as may be included within the scope of the invention as defined by the appended claims.

DETAILED DESCRIPTION OF THE PREFERRED EMBODIMENTS

Turning now to the drawings, it is understood that the use of terms "right", "left", "upper" and "lower" is with respect to the drawings and those terms are not to be construed as limiting the invention to any particular orientation of the drawings and of the depicted present invention.

Figure 1:
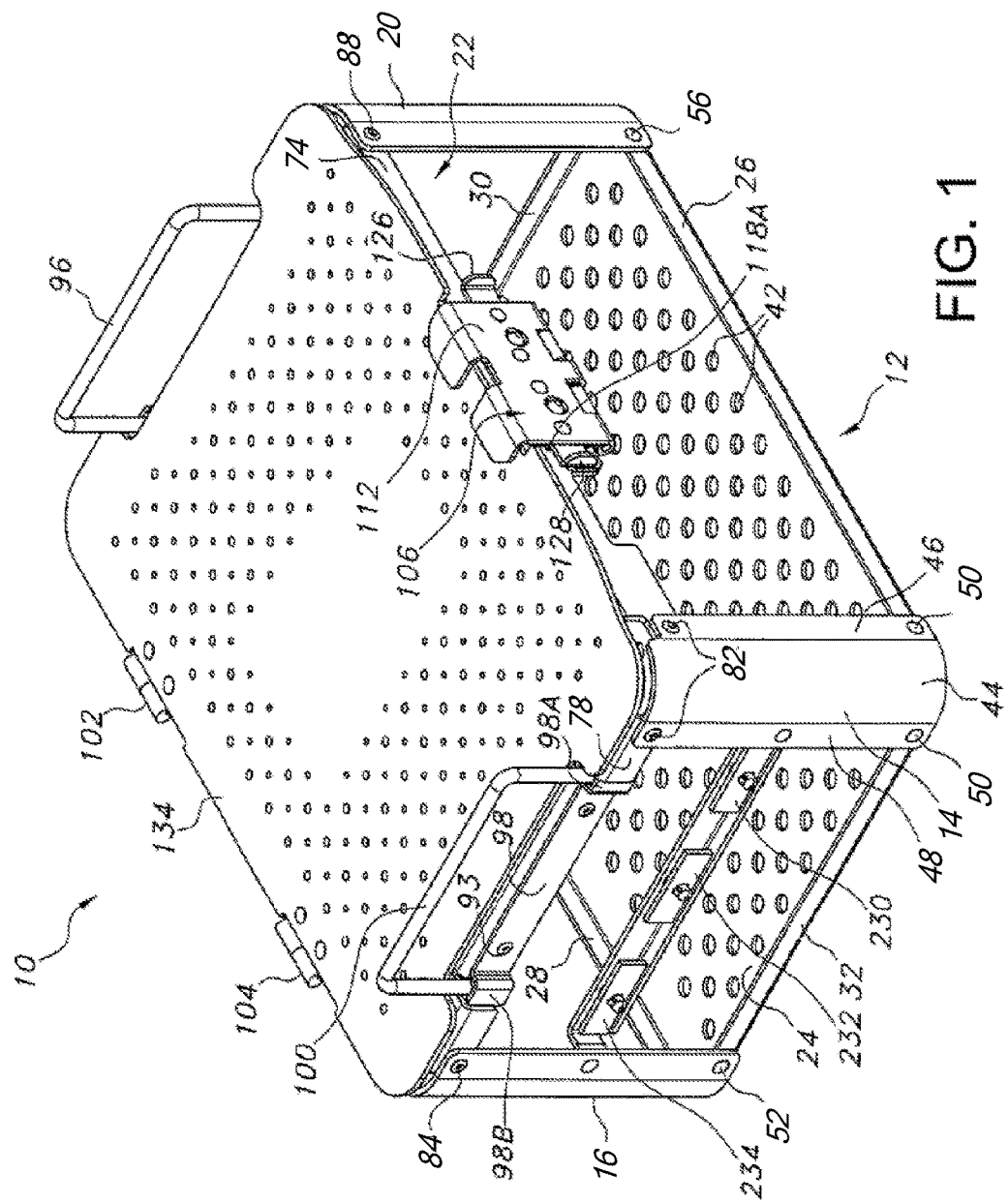
FIG. 1 is perspective view looking at the top of a screw tray 10 according to the present invention.

Thus, FIG. 1 is a perspective view of a containment case comprising a screw tray 10 and a detachable lid 134 according to the present invention. The screw tray 10 comprises a base plate 12 connected to the lower ends of four upstanding corner supports 14, 16, 18 and 20. Upper ends of the corner supports are connected to a generally rectangular-shaped main frame 22.

As particularly shown in FIGS. 1, 2, 7 to 9, 15, 16, 19, 23 and 24, the base plate 12 has a planar floor portion 24 extending to a right upstanding rim 26 opposite a left upstanding rim 28. An upper upstanding rim 30 resides between the right and left rims 26, 28. A lower upstanding rim 32 is opposite the upper rim 30 and intermediate the right and left rims 26, 28. The base plate 12 has a rectangular shape with the right and left rims 26, 28 being significantly longer than the upper and lower rims 30, 32.

A first curved corner 34 of the base plate 12 resides between the right and lower rims 26, 28, a second curved corner 36 resides between the lower and left rims 32, 28, a third curved corner 38 resides between the left and upper rims 28, 30, and a fourth curved corner 40 resides between the upper and right rims 30, 26. The base plate 12 is further provided with a plurality of openings or perforations 42 spaced inwardly of the rims 26, 28, 30 and 32, and curved corners 34, 36, 38 and 40.

As shown in FIG. 1, the corner supports 14, 16, 18 and 20 each comprise a curved portion 44 extending through an arc of about 90° in cross-section to opposed planar portions 46 and 48. In particular, rivets 50 connect the right rim 26 and the lower rim 32 adjacent to the curved corner 34 of the base plate 12 to the opposed planar portions at the lower end of the first corner support 14. Rivets 52 connect the lower rim 32 and the left rim 28 adjacent to the curved corner 36 to the opposed planar portions at the lower end of the second corner support 16. Rivets 54 connect the left rim 28 and the upper rim 30 adjacent to the curved corner 38 to the opposed planar portions at the lower end of the third corner support 18. Finally, rivets 56 connect the upper rim 30 and the right rim 26 adjacent to curved corner 40 to the opposed planar portions at the lower end of the fourth corner support 20.

The rectangular-shaped main frame 22 comprises opposed right and left frame walls 58 and 60 extending to and meeting with opposed upper and lower frame walls 62 and 64. The main frame 22 has a rectangular shape with the right and left frame walls 58 and 60 being significantly longer than the upper and lower frame walls 62 and 64.

Figure 4:
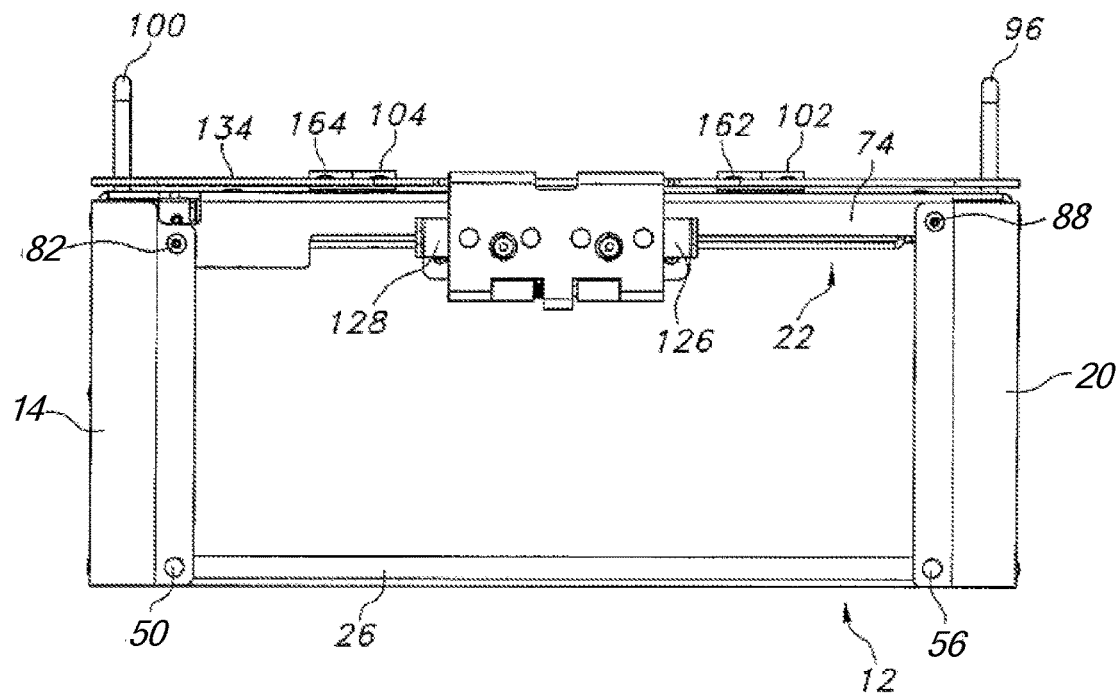
FIG. 4 is an elevational, right side view of the screw tray 10 shown in FIG. 1.

A first curved corner 66 joins the right frame wall 58 to the lower frame wall 64, a second curved corner 68 joins the lower frame wall 64 to the left frame wall 60, a third curved corner 70 joins the left frame wall 60 to the upper frame wall 62, and a fourth curved corner 72 joins the upper frame wall 62 to the right frame wall 58. Further, a right depending rim 74 (FIGS. 2, 4 and 8) extends downwardly from the right frame wall 58. A left depending rim 76 extends downwardly from the left frame wall 60. A lower depending rim 78 extends downwardly from the lower frame wall 64. And, an upper depending rim 80 extends downwardly from the upper frame wall 62.

Rivets 82 connect the right depending rim 74 and the lower depending rim 78 adjacent to the curved corner 66 of the tray frame 22 to the opposed planar portions at the upper end of the first corner support 14. Rivets 84 connect the lower depending rim 78 and the left depending rim 76 adjacent to the curved corner 68 to the opposed planar portions at the upper end of the second corner support 16.

Rivets 86 connect the left depending rim 76 and the upper depending rim 80 adjacent to the curved corner 70 to the opposed planar portions at the upper end of the third corner support 18. Finally, rivets 88 connect the upper depending rim 80 and the right depending rim 74 adjacent to curved corner 72 to the opposed planar portions at the upper end of the fourth corner support 20.

Figure 2:
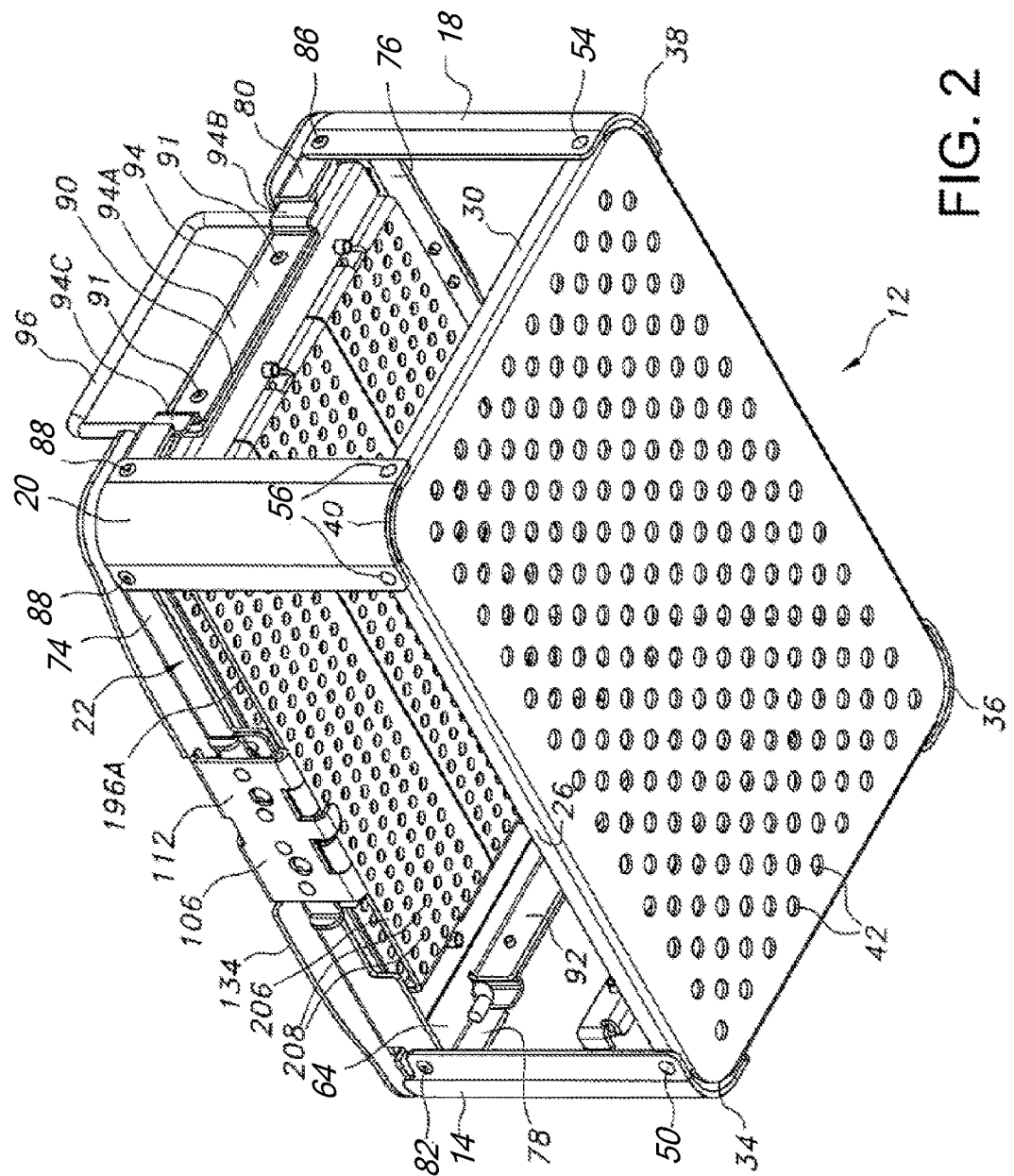
FIG. 2 is a perspective view looking at the base plate 12 of the screw tray 10 shown in FIG. 1.
Figure 3:
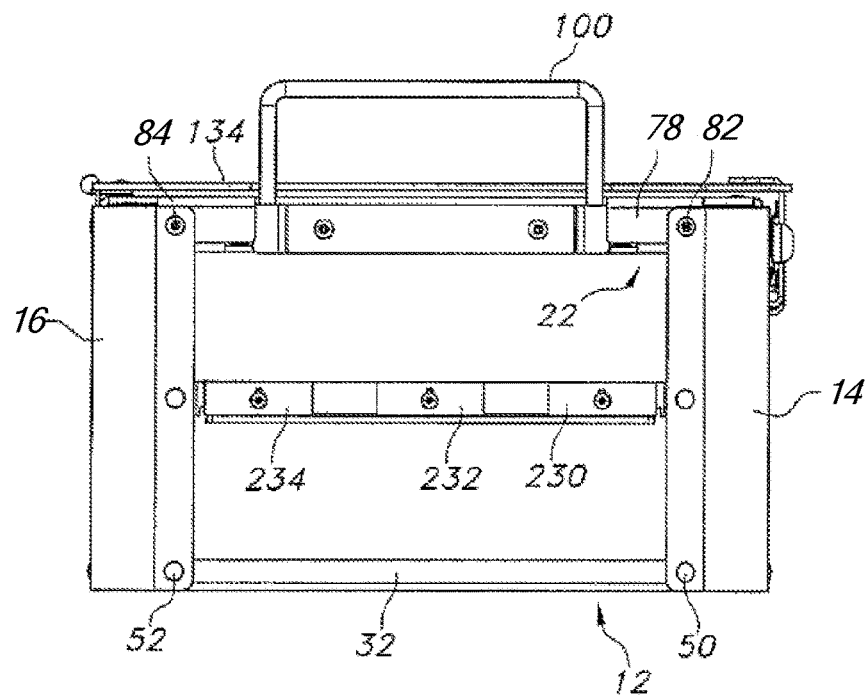
FIG. 3 is an elevational view looking at the lower end of the screw tray 10 shown in FIG. 1.

As shown in FIG. 2, middle portions of the downwardly depending upper rim 80 and upper frame wall 62 of the main frame 22 are bent in a downwardly direction to form an upper depending web 90. Similarly, middle portions of the downwardly depending lower rim 78 and lower frame wall 64 of the main frame 22 are bent in a downwardly direction to form a lower depending web 92. These webs 90 and 92 have opposed planar faces that are generally parallel to each other.

An upper handle bracket 94 comprises a middle planar bracket plate 94A extending to apposed L-shaped wings 94B and 94C. The middle bracket plate 94A is secured to the upper depending web 90 with rivets 91 so that its opposed L-shaped wings 94B and 94C reside behind opposed portions of the downwardly depending upper rim 80 on either side of web 90.

An upper or first bale handle 96 has a middle grip portion 96A extending to opposed depending legs 96B, 96C having respective outwardly extending feet 96D, 96E. The legs 96B, 96C are received in the space formed between the L-shaped wings 94B, 94C and the upper depending web 90. The outwardly extending feet 96D, 96E prevent the handle 90 from separating from the main tray frame 22, while allowing the handle to freely travel in both an upwardly and a downwardly direction for the length of the legs 96B, 96C.

Similarly, a lower handle bracket 98 comprises a middle planar bracket plate 98A extending to apposed L-shaped wings 98B and 98C. The middle bracket plate 98A is secured to the lower depending web 92 with rivets 93 so that its opposed L-shaped wings 98B and 98C reside behind opposed portions of the depending lower rim 64 of the lower portion of the main frame 22 on either side of the web 92.

Figure 8:
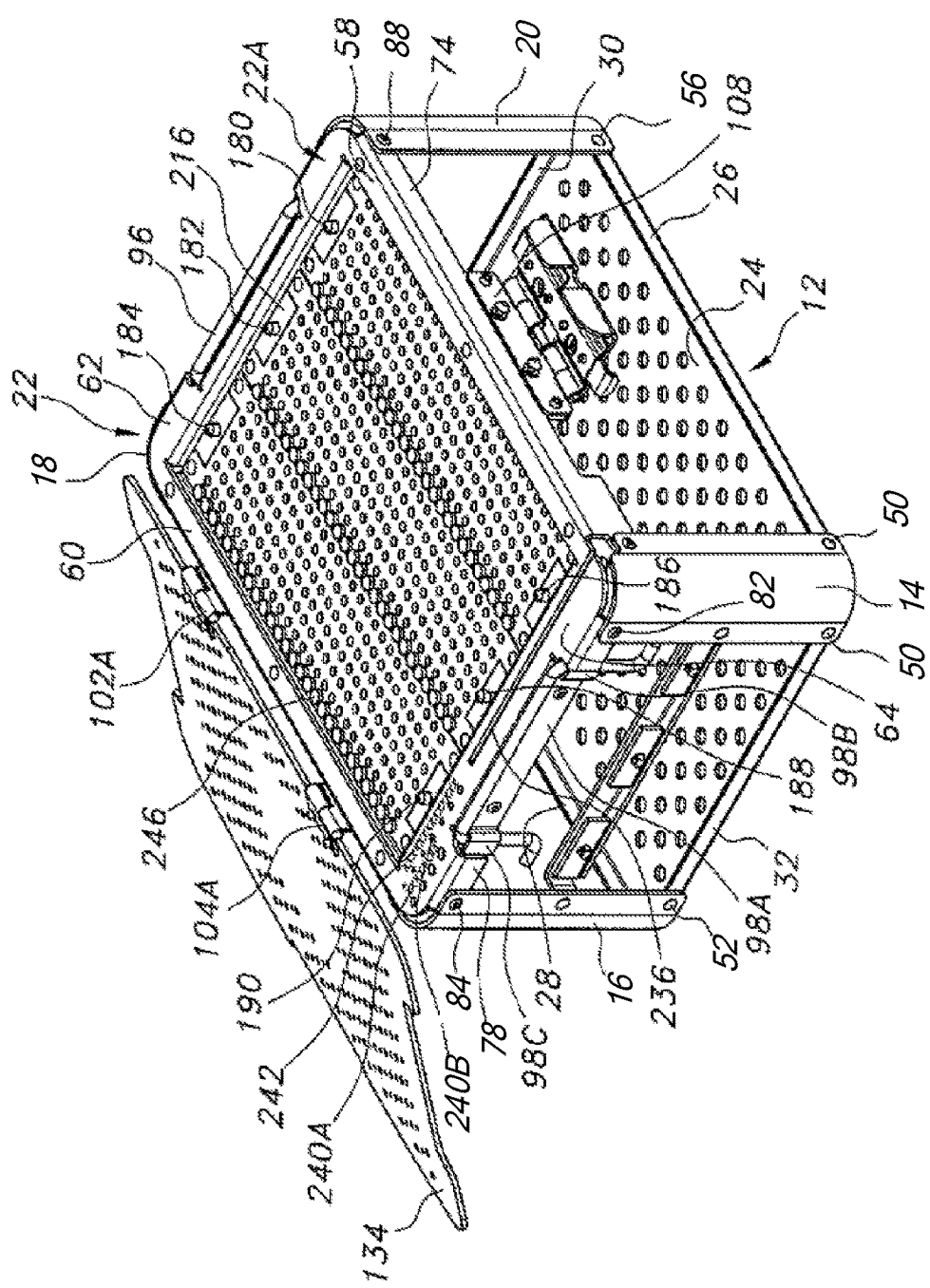
FIG. 8 is a perspective view of the screw tray 10 shown in FIG. 1 with the lid 134 in an opened position.
Figure 9:
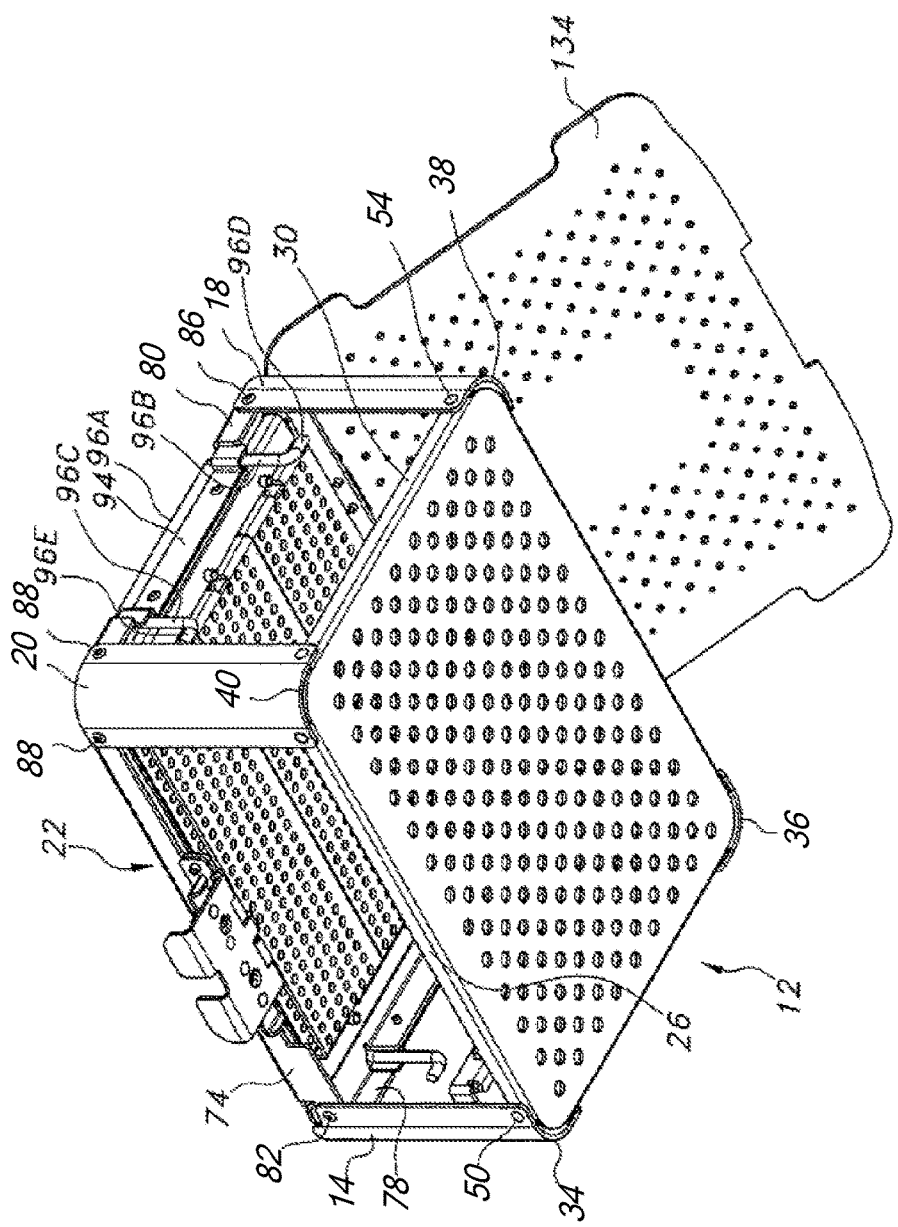
FIG. 9 is a perspective view looking at the base plate 12 of the screw tray 10 shown in FIG. 1, but with the lid 134 in an opened position as shown in FIG. 8.
Figure 10:
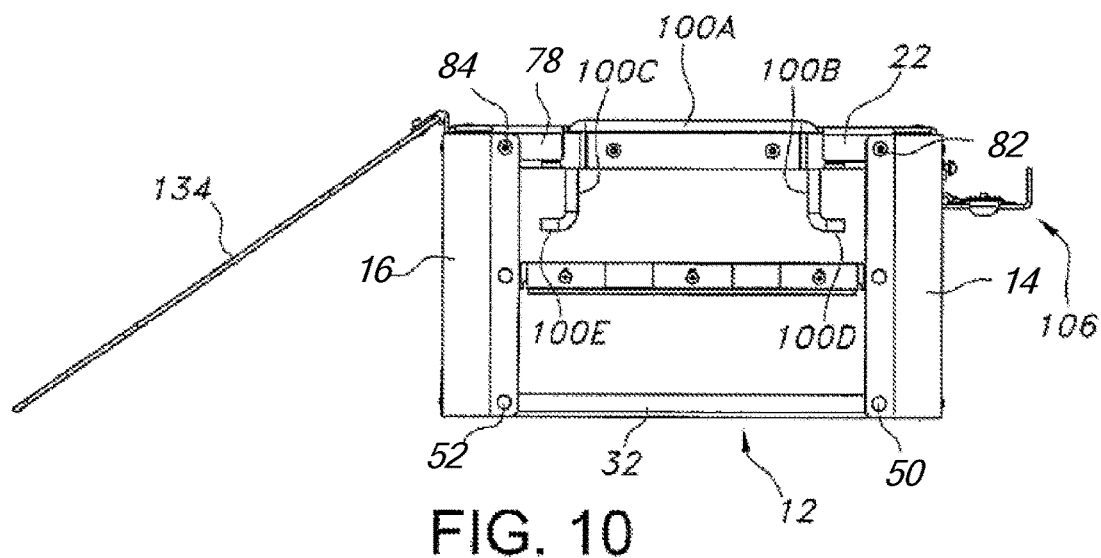
FIG. 10 is an elevational, lower end view of the screw tray 10 shown in FIG. 1, but with the lid 134 in an opened position as shown in FIG. 8.
Figure 11:
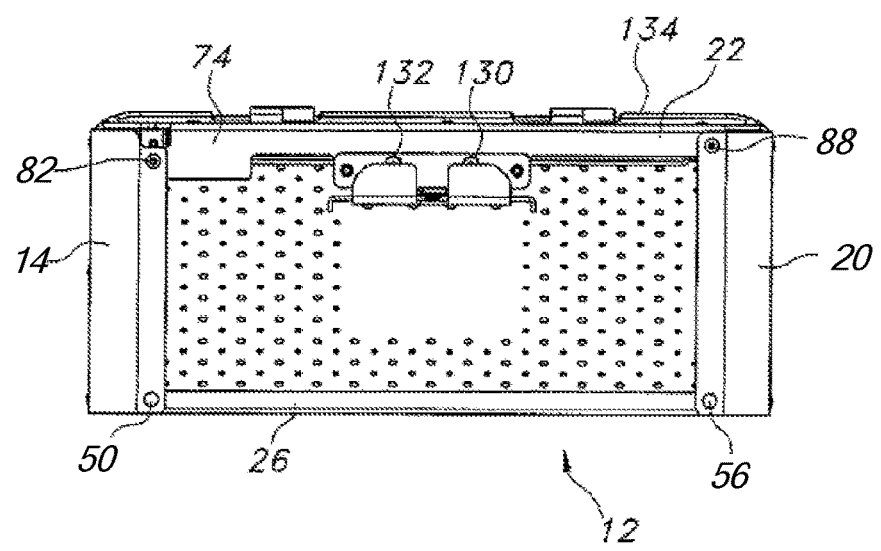
FIG. 11 is an elevational, right side view of the screw tray 10 shown in FIG. 10 with the latch 106 in an opened position.

FIGS. 8 and 10 show a lower or second bale handle 100 having a middle grip portion 100A extending to opposed depending legs 100B, 100C having respective outwardly extending feet 100D, 100E. Legs 100B, 100C are received in the space formed between the L-shaped wings 98B, 98C and the lower depending web 92. The outwardly extending feet 100D, 100E prevent the lower handle 100 from separating from the main tray frame 22 while allowing the handle to freely travel in both an upwardly and a downwardly direction for the length of the legs 100B, 100C.

Figure 5:
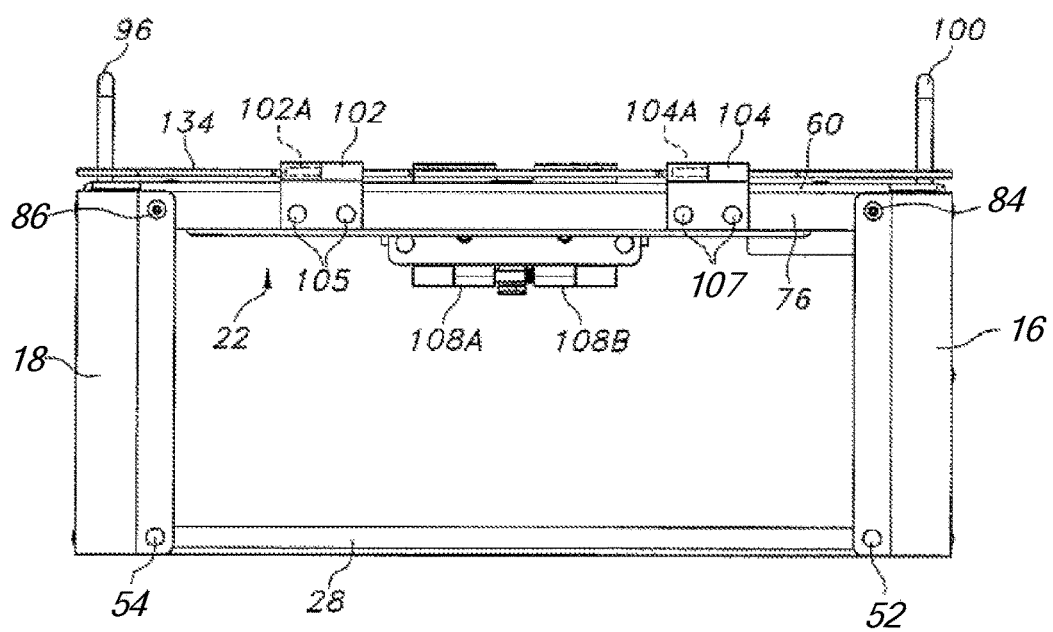
FIG. 5 is an elevational, left side view of the screw tray 10 shown in FIG. 1.

As shown in FIGS. 1 and 5, the depending rim 76 extending downwardly from the left frame wall 60 supports spaced-apart lid bracket 102 and 104. Lid bracket 102 is secured by rivets 105 to the left depending rim 76 adjacent to the upper frame wall 62. The other lid bracket 104 is secured by rivets 107 to the left depending rim 76 adjacent to the lower frame wall 64. The lid brackets 102 and 104 have respective upwardly extending portions supporting cantilever pivot pins 102A and 104A (FIG. 8). The pivots pins 102A, 104A are co-axial and space above an imaginary plane formed by the upper surface 22A of the tray frame 22.

Figure 12:
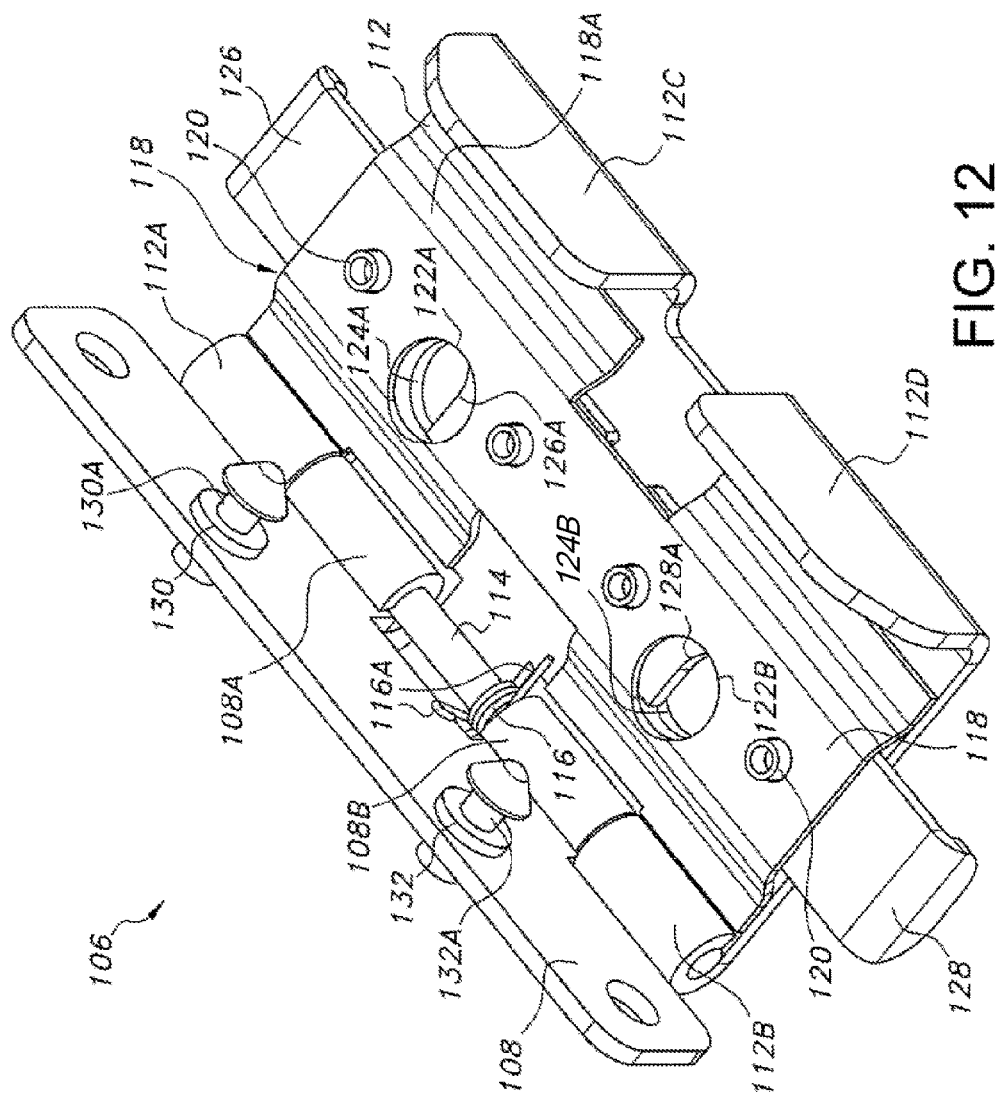
FIG. 12 is a perspective view of the latch 106 for the screw tray 10 shown in FIG. 1.
Figure 21:
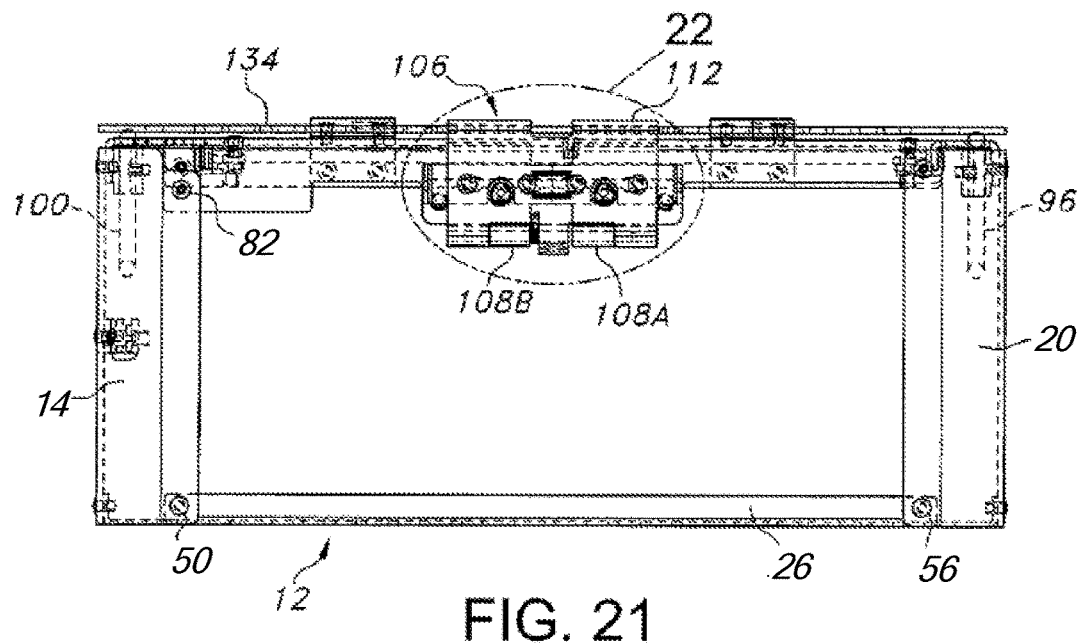
FIG. 21 is a right side elevational view of the screw tray 10 shown in FIG. 1, but with phantom details of the latch 106.
Figure 22:
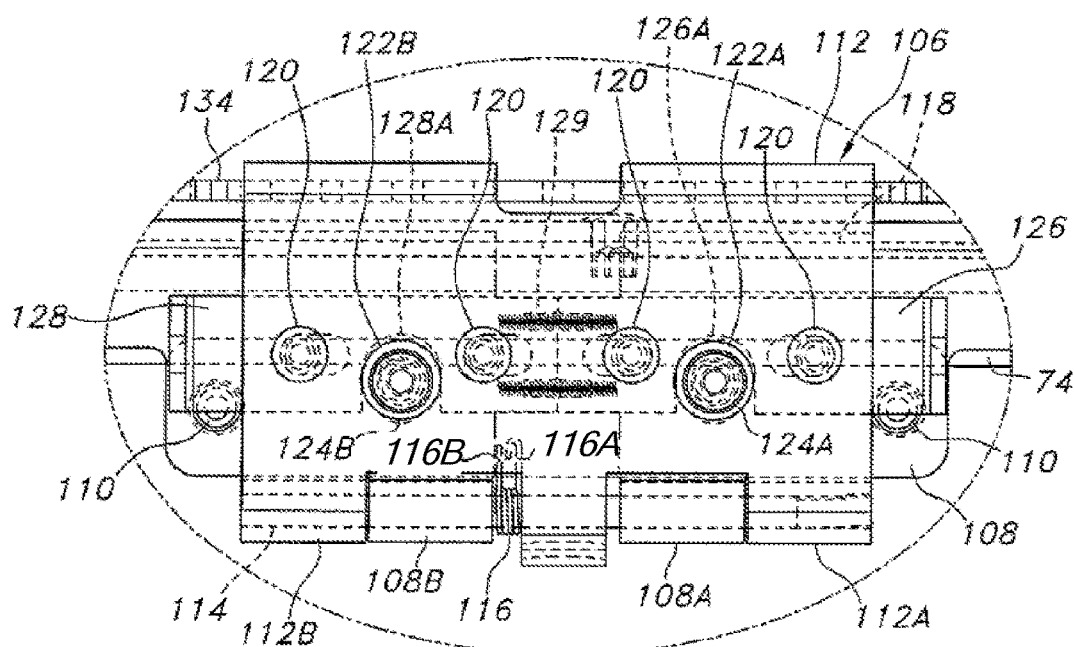
FIG. 22 is an enlarged view of the indicated area in FIG. 21.

The depending rim 74 extending from the right frame wall 58 has a greater depending length than the opposed depending rim 76 supporting the lid brackets 102, 104. That is because the right depending rim 74 supports a latch 106. As shown in FIGS. 12, 21 and 22 among other drawings, latch 106 comprises a fixed plate 108 secured to the depending rim 74 by spaced apart rivets 110. A lower edge of the fixed plate 108 forms a first pair of spaced apart co-axial sleeves 108A and 108B. A latch plate 112 comprises a second pair of spaced apart co-axial sleeve 112A and 112B. A pivot pin 114 is received in the first and second pairs of co-axial sleeves 108A, 108B and 112A, 112B to thereby pivotably secure the latch plate 112 to the fixed plate 108.

A coil spring 116 is supported on the pivot pin 114 in the gap between the first pair of co-axial sleeves 108A, 108B. The coil spring 116 has outwardly extending legs 116A, 116B. Spring leg 116A is biased against the fixed plate 108 while spring leg 116B is biased against the latch plate 112. In that manner, the coil spring 116 biases the latch plate 112 is an open position, spaced from the fixed plate 108 and the main tray frame 22.

A release bracket 118 faces the fixed plate 108 and is secured to the latch plate 112 by four spaced-apart rivets 120. The release bracket 118 has two spaced apart openings 122A and 122B that align with similarly sized spaced apart openings 124A and 124B through the latch plate 112. Opposed finger activated release legs 126 and 128 are housed in the space between the trough 118A of the release bracket 118 and the back face of the latch plate 112. The release legs 126, 128 are provided with respective openings 126A and 128A. A biasing coil spring 129 is also housed in the space between the release bracket trough 118A and the latch plate 112. This coil spring biases against the release legs 126 and 128 so that with the coil spring in an uncompressed state, the openings 126A, 128A in the release legs 126 and 128 are partially blocked by the aligned openings 122A, 124A and 122B, 124B in the respective release bracket 118 and in the latch plate 112.

The fixed plate 108 is further provided with a pair of spaced-apart bullet-shaped protrusions 130 and 132, each having an annular recess 130A, 132A. That way, the latch plate 112 is releasably secured to the fixed plate 108 when the latch plate is moved toward the fixed plate with the bullet protrusions 130, 132 extending into the openings 126A, 128A in the release legs 126, 128 until the bullet protrusions contact the release legs, which causes the legs to move in a lateral direction toward each other and against the bias of the latch coil spring. This movement causes the openings 126A, 128A in the release legs to align with the spaced-apart openings 122A, 122B in the release bracket 118 and with the spaced-apart openings 124A, 124B in the latch plate 112. Continued movement of the latch plate 112 toward the fixed plate 108 causes the coil spring to bias the release legs 126, 128 in an outwardly lateral direction back toward their original positions and into engagement with the annular recesses 130A, 132A of the bullet protrusions 130, 132. With the latch plate 112 thus secured to the fixed plate 108, a pair of inwardly extending feet 112C, 112D of the latch plate 112 reside spaced above the right side 58 of the tray frame 22. The significance of this will be described hereinafter.

While not shown in the drawings, the release legs 126 and 128 also have respective openings that receive the outermost two rivets 120. These openings are oval-shaped and of sufficient length to allow for the back and forth lateral movement of the release legs 126, 128 while the rivets 120 prevent the legs from separating from their position between the latch plate 112 and release bracket 118.

Various ones of the drawing figures illustrate a plate-shaped lid 134 of the screw tray 10. As particularly shown in FIG. 6, lid 134 has spaced apart right and left lid edges 136 and 138 extending to and meeting with upper and lower lid ends 140 and 142. A curved edge 144 resides between the right and lower edges 136, 142, a curved edge 146 resides between the lower and left edges 142, 138, a curved edge 148 resides between the left and upper edges 138, 140, and a curved edge 150 resides between the upper and right edges 140, 136.

Figure 6:
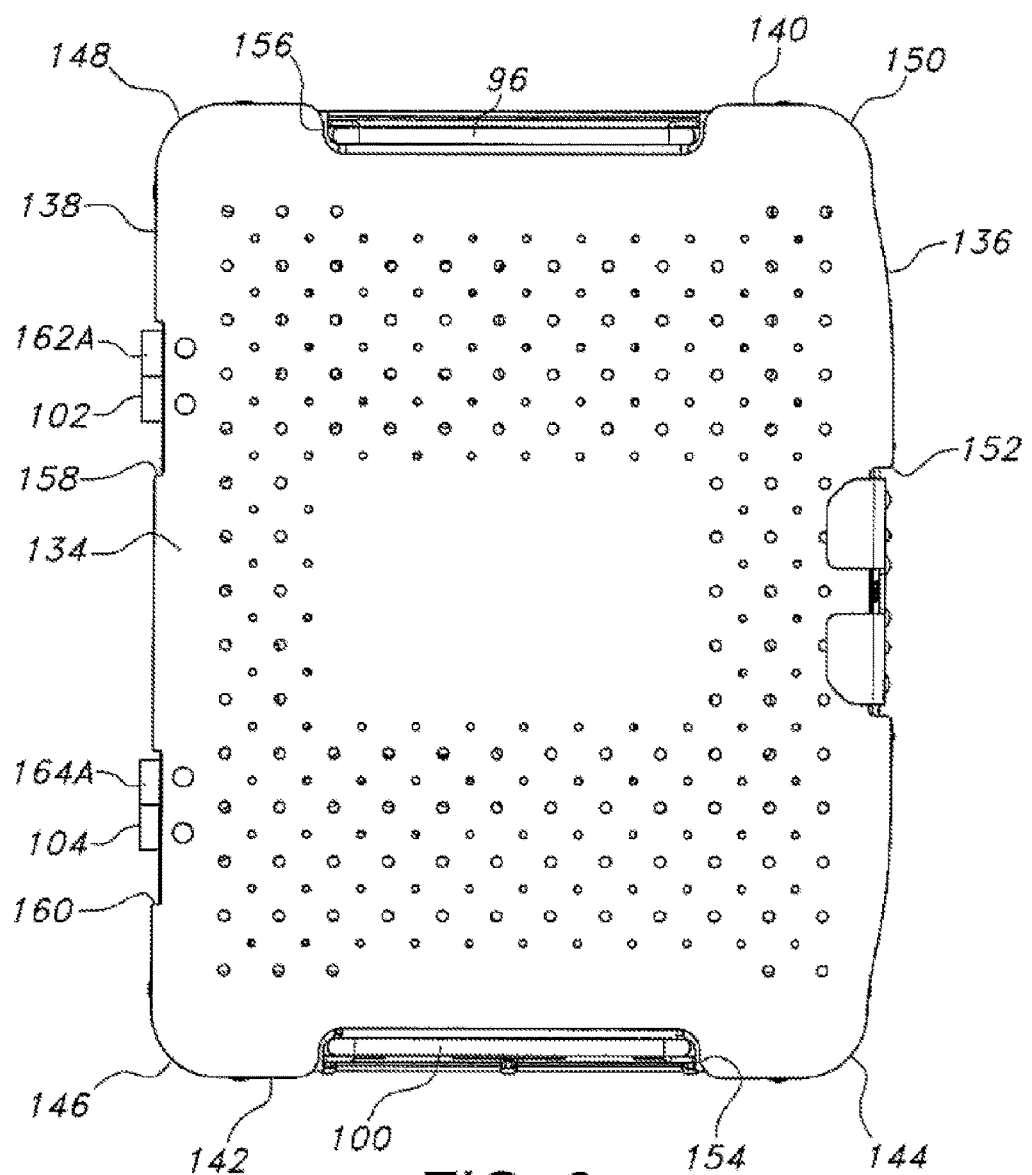
FIG. 6 is a plan view of the screw tray 10 shown in FIG. 1 with the lid 134 in a closed position.
Figure 7:
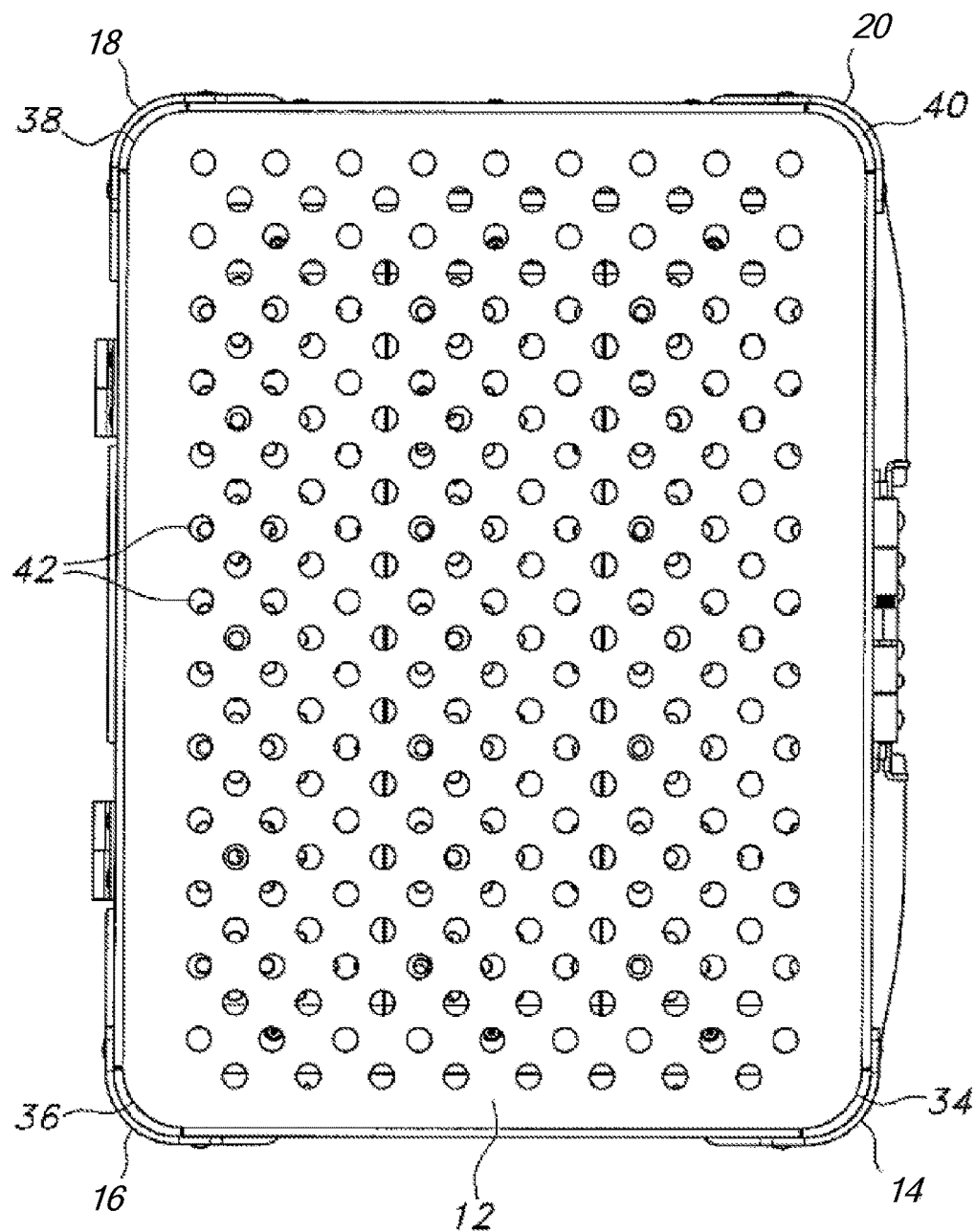
FIG. 7 is a plan view looking at the base plate 12 of the screw tray 10 shown in FIG. 1.

FIG. 6 further shows that a right squared-off U-shaped inlet 152 resides in the right edge 136, a lower squared-off U-shaped inlet 154 resides in the lower edge 142, and an upper squared-off U-shaped inlet 156 resides in the upper edge 140. A pair of spaced apart squared-off U-shaped inlets 158 and 160 resides in the left edge 138. The lid supports a pair of sleeve plates 162, 164 having respective open ended sleeves 162A and 164A aligned co-axially with each other.

The lid 134 is pivotably mounted on the tray frame 22 with the cantilever pivot pins 102B, 104B (FIG. 5) of brackets 102, 104 received in the sleeves 162A and 164A of the respective lid brackets 162 and 164. With the lid 134 connected to tray frame 22 in this manner, the lid is pivotable between a fully opened position shown in FIGS. 8 to 10, 13 to 16 and 23 and a closed position shown in FIGS. 1 to 6 and 19. As previously described, the lid 134 is retained in the closed position by the latch 106 when the fixed plate 108 is secured to the latch plate 112 by movement of the release legs 126, 128 engaging the annular recesses 130A, 132A of the respective bullet protrusions 130, 132. In the closed position, the latch plate 112 is received in the right squared-off U-shaped inlet 152 and the pair of inwardly extending latch feet 112C, 112D resides over the lid 134. With the lid 134 in the closed position, the upper bale handle 96 is received in the upper lid inlet 154 and the lower bale handle 100 is received in the lower lid inlet 154.

To move the lid 134 from the closed to the opened position, a user manually squeezes the release legs 126, 128 toward each other until their openings 126A, 128A align with the openings 122A, 122B in the release bracket 118 and with the openings 124A, 124E in the latch plate 112, thereby releasing the legs 126, 128 from engagement with the annular recesses 130A, 132A of the bullet-shaped protrusions 130, 132. The lid 134 can now be moved with the cantilever pivot pins 102B, 104B pivoting in the sleeves 162A and 164A of the respective lid brackets 162, 164.

Figure 15:
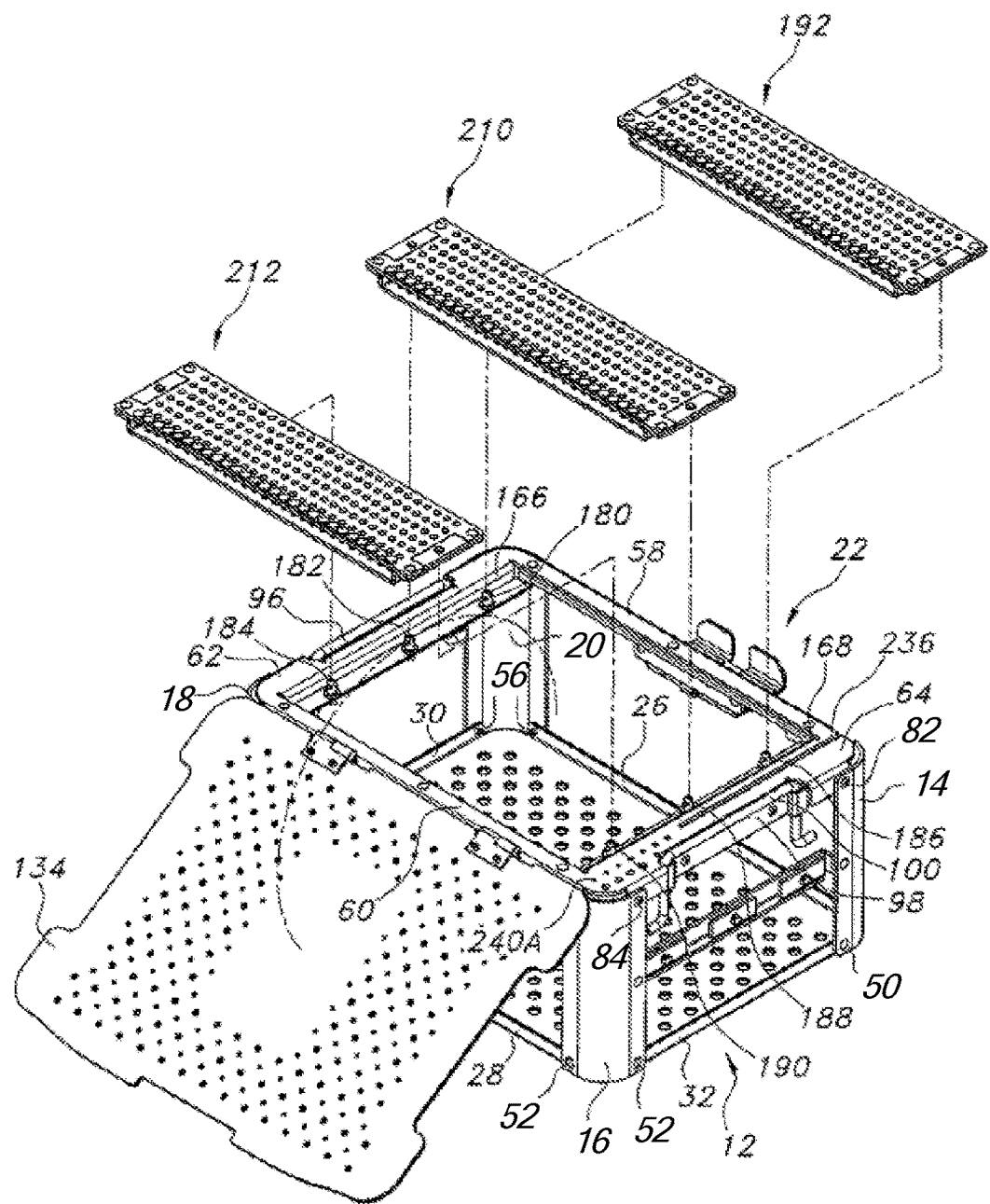
FIG. 15 is a perspective view of the screw tray 10 shown in FIG. 1, but with the lid 134 in an open position and with screw decks 192, 210 and 212 separated from the tray frame 22.
Figure 16:
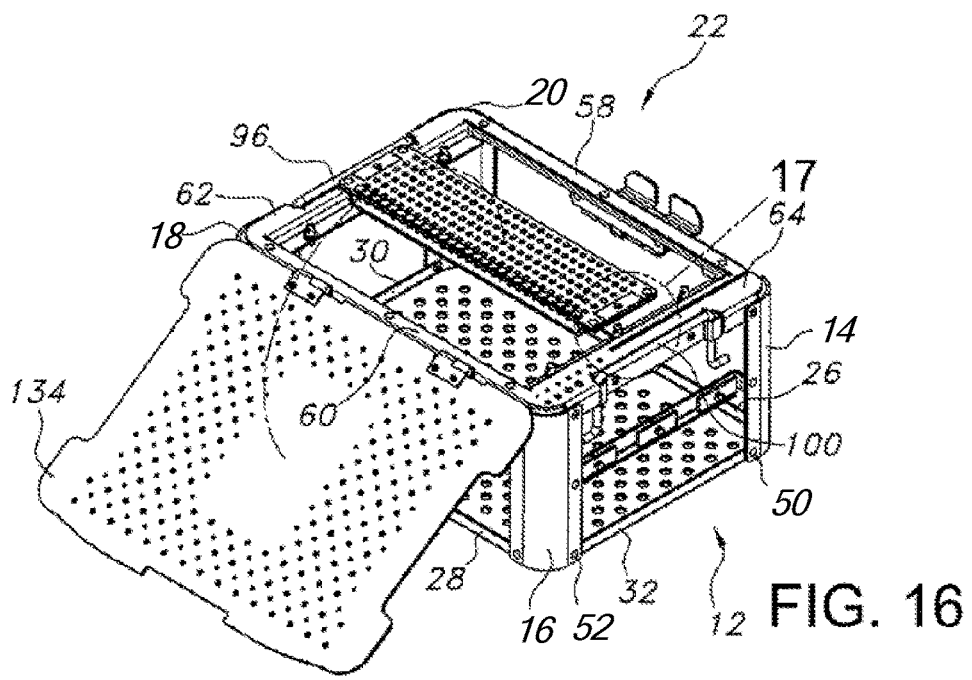
FIG. 16 is a perspective view of the screw tray 10 shown in FIG. 15, but with screw deck 210 being moved into engagement with the tray frame 22.

As shown in FIG. 15, the upper side 62 of the tray frame 22 has an inner depending rim 166. Similarly, the lower side 64 of the tray frame has an inner depending rim 168. The right and left sides 58, 60 of the tray frame 22 are not provided with similar inner depending rims.

Figure 17:
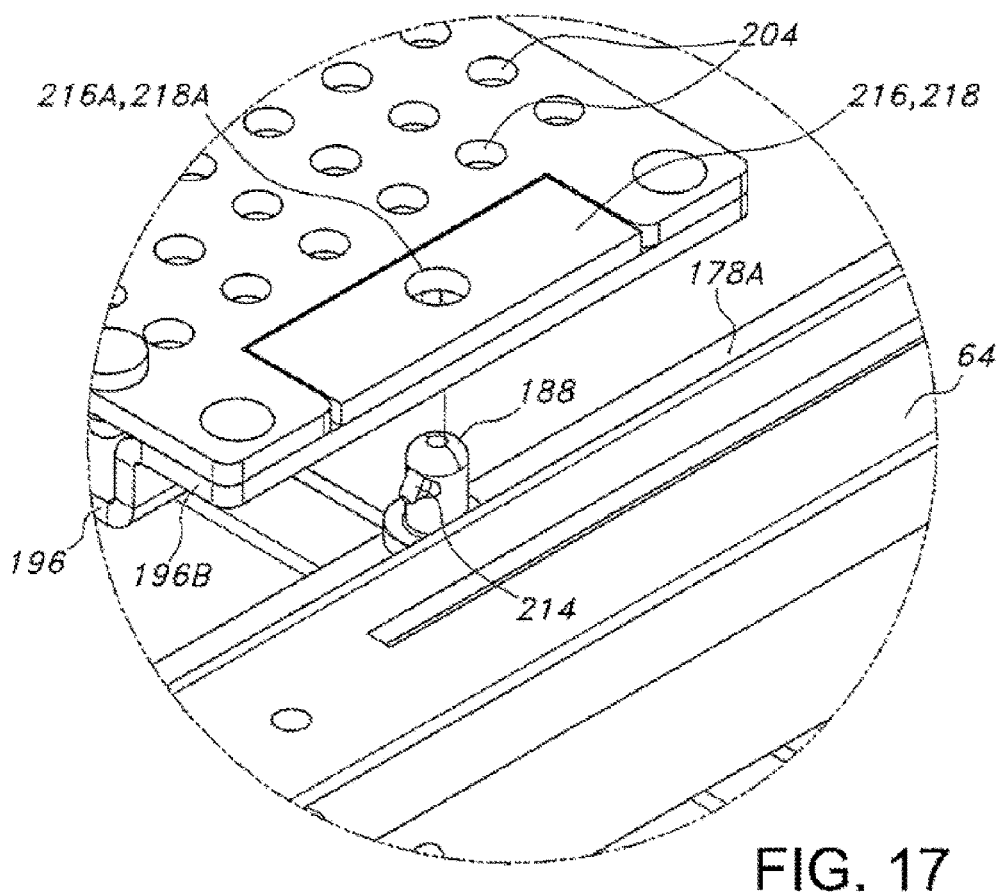
FIG. 17 is an enlarged view of the indicated area from FIG. 16.
Figure 23:
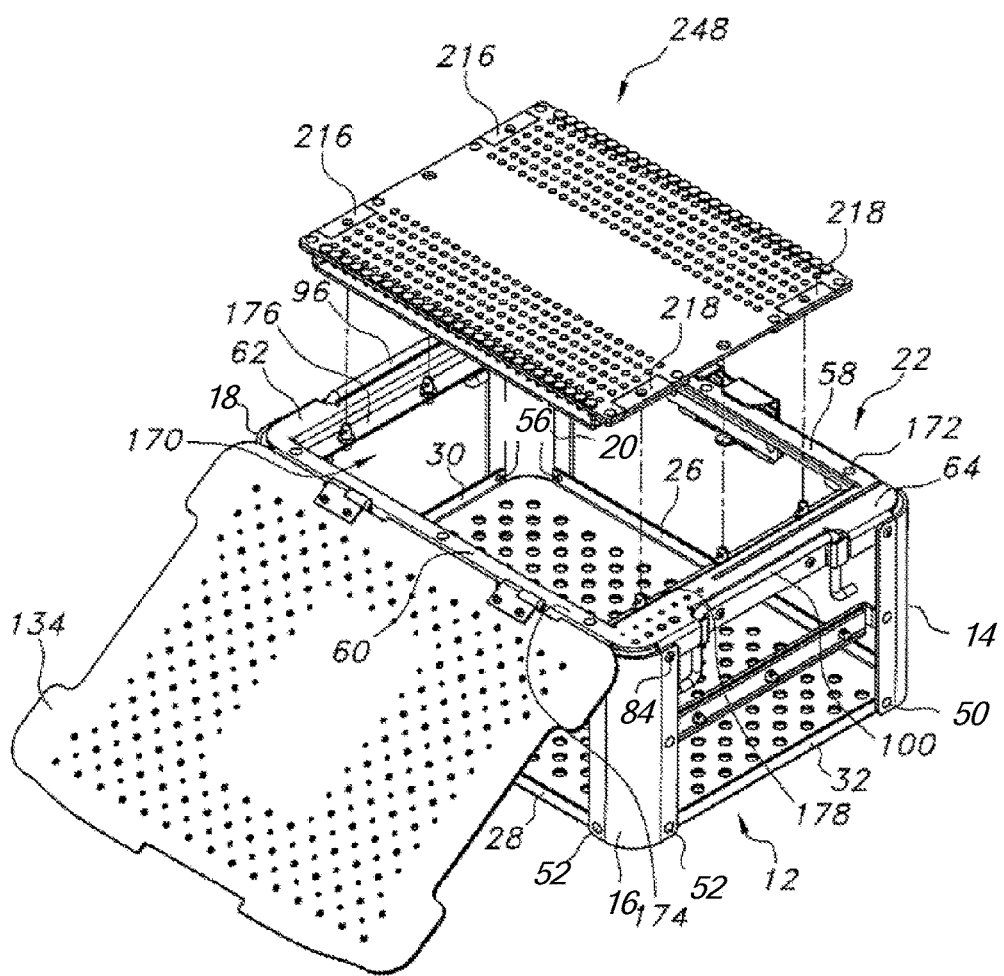
FIG. 23 is a perspective view of the screw tray 10 shown in FIG. 1, but with a single screw deck 248 occupying the area of the tray frame 22 shown occupied by screw decks 192, 210 and 212 in FIGS. 8, 9, 13 and 15.

As particularly shown in FIG. 23, a screw deck frame 170 is supported by the tray frame 22. The screw deck frame 170 has a generally rectangular shape and comprises spaced apart right and left frame sides 172 and 174 extending to and meeting with upper and lower frame sides 176 and 178. The screw deck frame 170 has a rectangular shape with the right and left frame sides 172 and 174 being significantly longer than the upper and lower frame sides 176 and 178. The right frame side 172 has a planar portion joined to an inner downwardly depending right portion. Similarly, the left frame side 174 has a planar portion joined to an inner downwardly depending left portion. The upper frame side 176 comprises an upper cross-bar portion that connects to depending portions of the right and left frame sides adjacent to the upper tray frame portion 62. As shown in FIG. 17, the lower frame side 178 comprises a lower cross-bar portion 178A that connects to depending portions of the right and left frame sides adjacent to the lower tray frame portion 64.

Among other drawings, FIG. 8 illustrates that three spaced apart pins 180, 182 and 184 extend upwardly from the upper cross-bar of the screw deck frame 170. Similarly, three spaced apart pins 186, 188 and 190 extend upwardly from the lower cross-bar 178A. Pin pairs 180 and 186 are aligned with each other as are pin pairs 182 and 188, and pin pairs 184 and 190.

Figure 18:
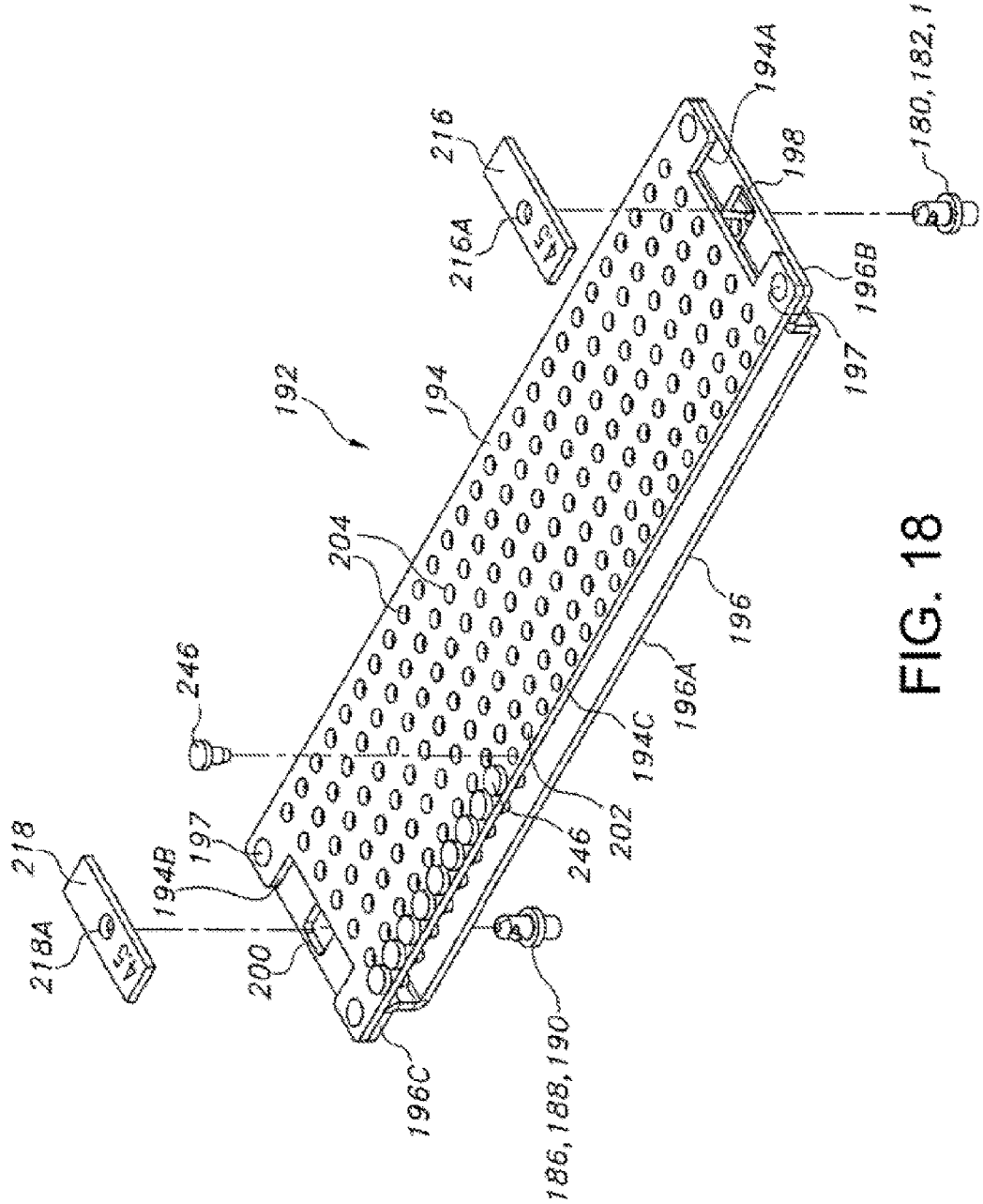
FIG. 18 is an exploded view showing the structure for connecting an exemplary screw deck 192 to a frame post.

Among other drawings, FIG. 18 illustrates an exemplary screw deck 192 comprising an upper planar plate 194 secured to a lower plate 196 by rivets 197. The upper plate 194 has opposed upper and lower inlets 194A, 194B. The lower plate 196 has a central planar portion 196A extending to spaced-apart upper and lower upwardly extending webs joined to respective planar lips 196B and 196C. The upper and lower lips 196B and 196C are co-planar. A centrally located opening 198 is provided inwardly of an edge of the upper planar lip 196B and into the upper upwardly extending web. Similarly, a lower centrally located opening 200 is provided inwardly from an edge of the lower planar lip 196C and into the lower upwardly extending web. Depending where the screw deck 192 is supported on the frame 170, the centrally located openings 198 and 200 receive one of the respective pin pairs 180 and 186, 182 and 188, and 184 and 190.

Moreover, the upper plate 194 of the exemplary screw deck 192 is provided with a column of first openings 202 running along the side 194C and a pattern of second openings 204 arranged in rows and columns throughout the remainder of the plate. Similarly, the central planar portion 196A (FIG. 2) of the lower deck plate 196 has a column of first openings 206 adjacent to one of its major sides and a pattern of second openings 208 arranged in rows and columns throughout the remainder of the lower deck plate. The first openings 202 in the upper plate are aligned one above the other with the first openings 206 in the lower deck plate 196. Similarly, the pattern of columns and rows of second openings 204 in the upper plate 194 are aligned one above the other with the second openings 208 in the lower plate 196. In one embodiment, the second openings in the upper and lower deck plates are arranged in at least two columns, each column having from 2 to 30 openings. In another embodiment, the second openings in the upper and lower deck plates are arranged in from two to seven columns, each column having from 2 to 30 openings. Further, the first and second openings in the upper deck plate are of the same or different size.

FIG. 15 further illustrates an exemplary second screw deck 210 and a third screw deck 212 according to the present invention. Screw decks 210 and 212 are similar to the first screw deck 192 in structure and function. With the first screw deck 192 supported on the screw deck frame 170 and received on pins 180, 186, the second screw deck 210 receive pins 182 and 188. Similarly, pins 184 and 190 receive the third screw deck 192 supported on the screw deck frame 170.

As particularly shown in FIG. 17, exemplary upstanding post 188 is provided with a spring loaded catch 214. Which pair of upstanding posts 180 and 186, 182 and 188, and 184 and 190 is received in corresponding openings 198 and 200 in the lower plate 196 depends on where on the screw deck frame 170 a particular screw deck 192, 210 and 212 is supported.

Further, FIGS. 17 and 18 show that rectangular-shaped indicia or label plates 216 and 218 are received in the respective upper and lower centrally located inlets 194A and 194B of exemplary plate 192. Label plate 216 has an opening 216A that is sized to receive one of the first posts 180, 182 and 184 with the spring-loaded catch 214 contacting the plate 216. Label plate 216 in turn contacts the lower screw deck plate 196 secured to the upper deck plate 194. Similarly, the rectangular-shaped label plate 218 has an opening 218A that is sized to receive one of the second upstanding posts 186, 188 and 190 with the spring loaded catch 214 contacting the plate. The label plate 218 in turn contacts the lower screw deck plate 196. In that manner, the screw decks 192, 210 and 212 are secured in place by the opposed indicia or label plates 214 and 216 held or retained on top of and in contact with the opposed ends of the lower plate 196 of the screw deck by spring-loaded catches 214.

Figure 19:
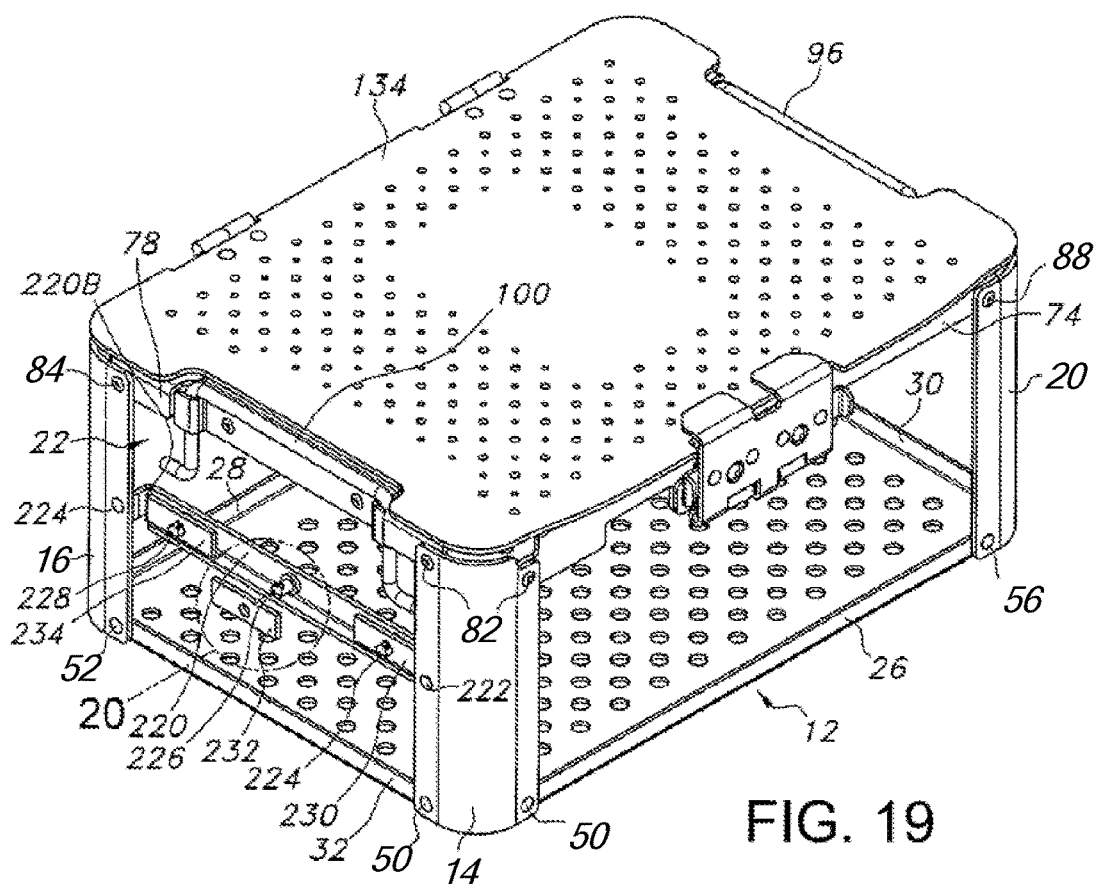
FIG. 19 is a perspective view of the screw tray 10 shown in FIG. 1 with an additional deck tray locking plate 232 being secured to an auxiliary deck plate cross-bar 220.
Figure 20:
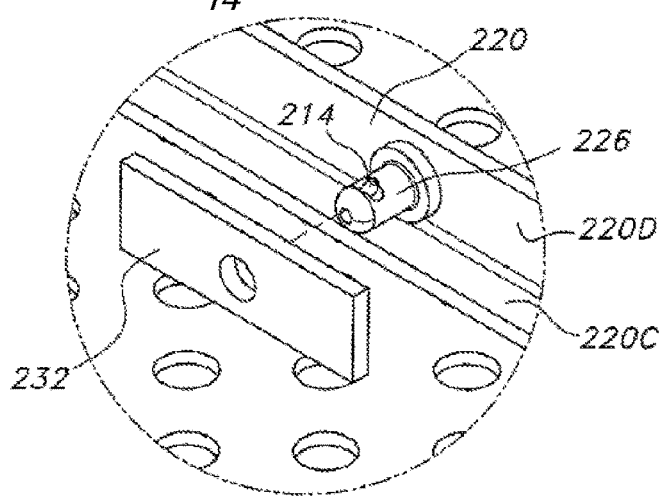
FIG. 20 is an enlarged view of the indicated area shown in FIG. 19.

Among other drawings, FIGS. 19 and 20 illustrate that a cross-bar 220 extends from the first corner support 14 to the second corner support 16 about half-way between the base plate 12 and the tray frame 22. Cross-bar 220 has an elongated U-shape with a first leg 220A secured to the first corner support 14 by rivet 222 and an opposed second leg 220B secured to the second corner support 16 by rivet 224. Cross-bar 220 has a horizontally aligned ledge 220C intermediate the opposed legs 220A, 220B. The cross-bar 220 is joined to a vertically aligned bar section 220D that supports a plurality of upstanding posts, for example ports 224, 226 and 228, which are similar to the previously described posts 180, 182, 184, 186, 188 and 190. These posts 224, 226 and 228 also include spring loaded catches 214 that retain additional respective indicia or indicia plates 230, 232 and 234 received thereon.

Figure 13:
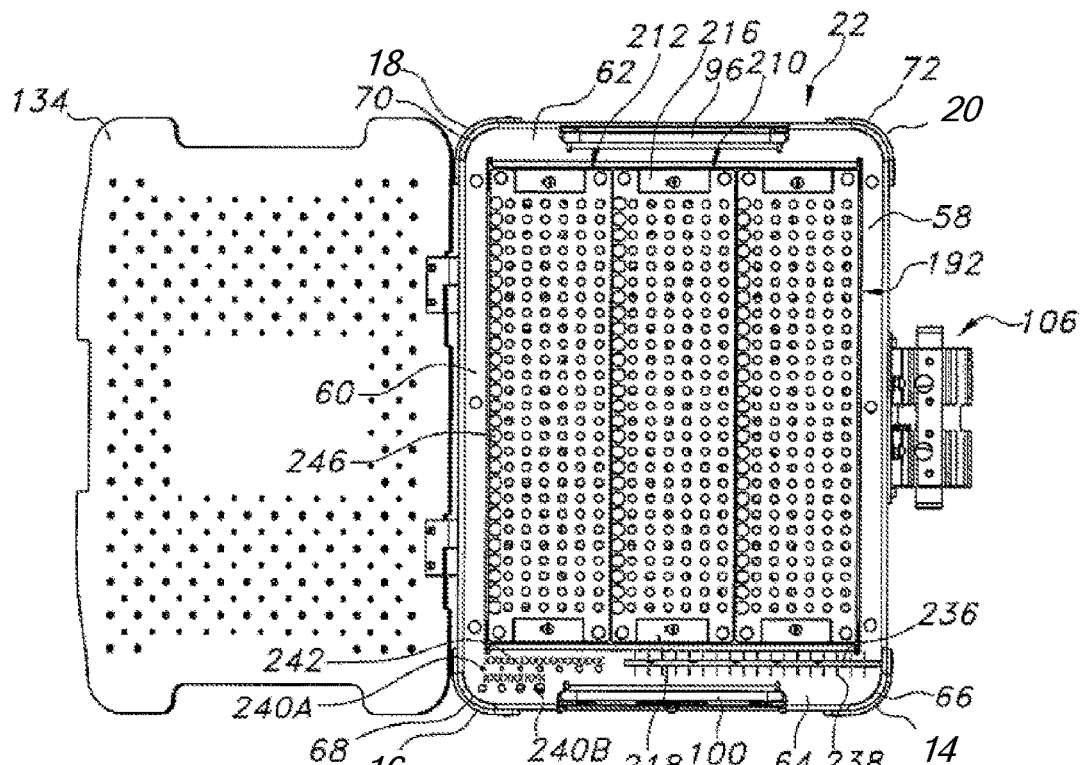
FIG. 13 is a plan view looking at the screw tray shown in FIG. 1, but with the lid 134 in an opened position so that screw deck plates 192, 210 and 212 are visible.
Figure 14:
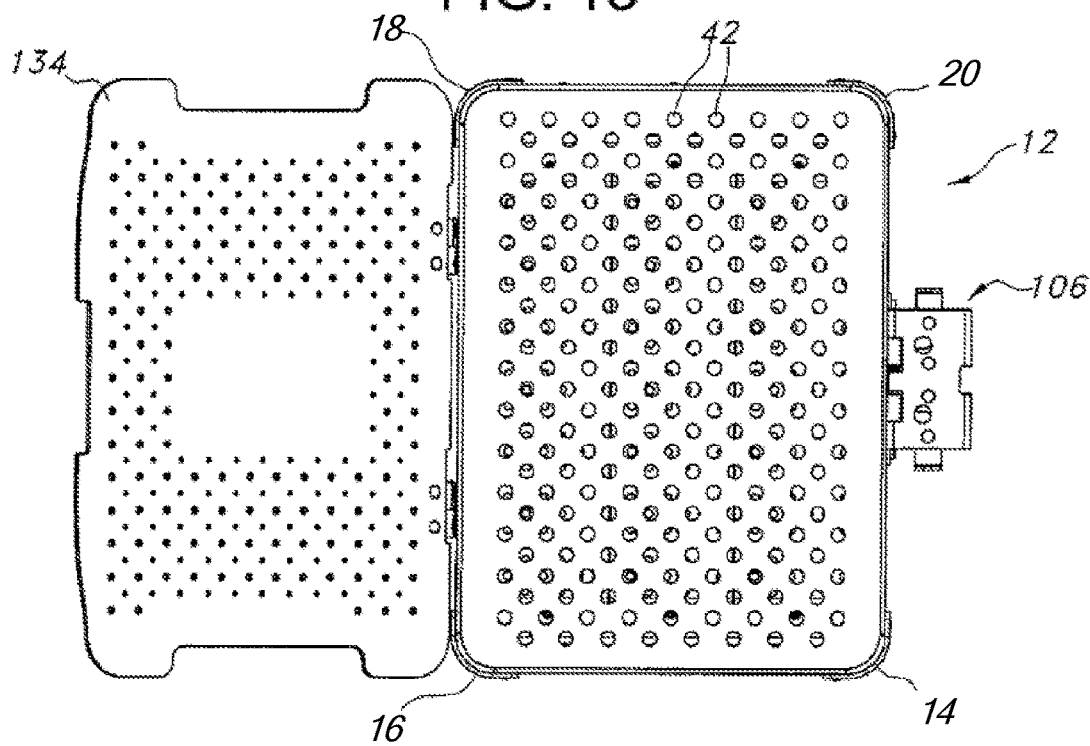
FIG. 14 is a plan view looking at the base plate 12 of the screw tray 10 shown in FIG. 13 with the lid 134 and latch 106 in open positions.

Among other drawings, FIG. 13 shows that the lower frame wall 64 of the tray frame 22 has an elongated, but narrow inlet 236 extending part-way along its length. A series of indicia marks 238 is provided at spaced intervals along either side of the inlet 236. Preferably these indicia marks are space at millimeter or multiples millimeter intervals from each other.

FIG. 13 further shows that the lower frame wall 64 of the tray frame 22 has a pattern of openings 240A to 240B with accompanying indicia 242. Openings 240A to 240B are of progressively larger diameters from a smallest diameter 240A to a largest diameter 240B. These openings are arranged in two rows adjacent to the elongated inlet 236.

In Use

Figure 25:
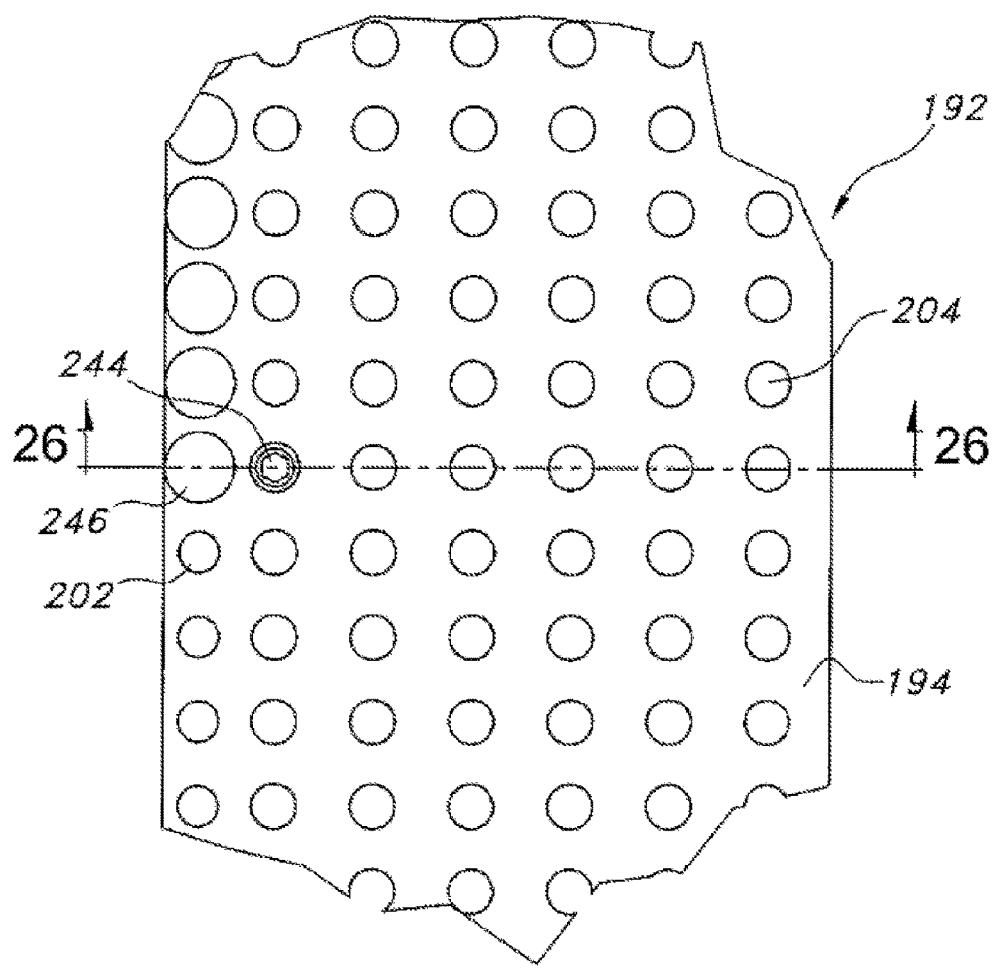
FIG. 25 is a plan, cut-away view of an exemplary screw deck 192 showing a removable insert 246 received in opening 202 and a screw 244 received in opening 204.
Figure 26:
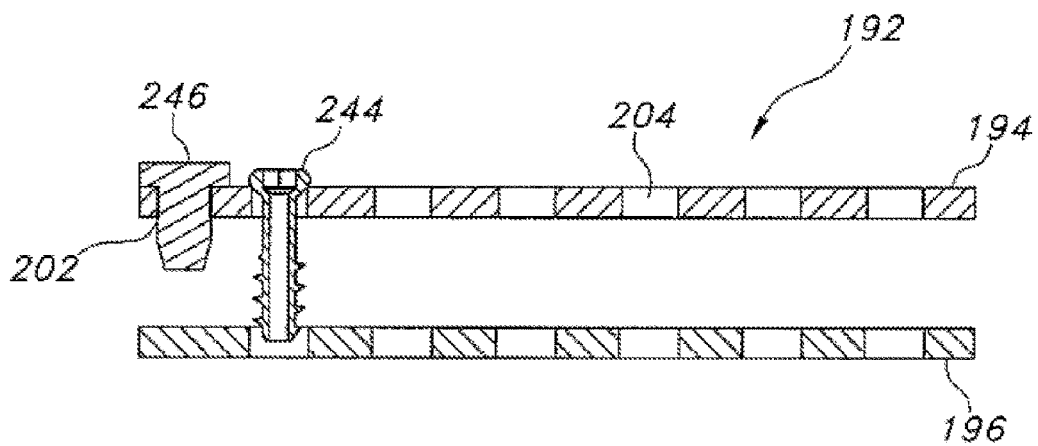
FIG. 26 is a cross-sectional view taken along line 26-26 in FIG. 25.

In use, the screw tray 10 is provided with a variety of surgical screws (FIGS. 25 and 26). The silicon inserts 246 are removably fit into openings 202 in the upper deck plate 194 are provided with a number, for example 10, 20, 30 . . . to 100, or 12, 14, 16, 18 . . . in millimeters (mm). This indicates the length of the screw 244 in the row immediately next to the insert 246 (exemplary screw lengths can also range from ¼ inch to about 4.5 inches). Thus, it is recognized that not every surgical screw may be long enough to extend through a second opening 204 in the upper plate 194 and into a second opening 208 in the lower deck plate. However, most surgical screws will have sufficient length so that being received in aligned openings in both the upper and lower plates adds support.

In an alternate embodiment, since the silicon inserts are not long enough to touch the lower deck plate 196, the column of first openings 206 in the lower plate is not needed.

The plates 216 and 218 are provided with labels that refer to the type of surgical screw contained in a particular screw deck 192, 210 and 212. An exemplary label 216, 218, 230, 232 and 234 for a plate 192, 210 and 212 will read "3.5 cannulated" for screws having cannulated threads with a 3.5 mm diameter. A plate labeled "4.5 cannulated" indicates that cannulated screws having a 4.5 mm diameter populate the associated screw deck. A plate labeled "3.5 cortical" is associated with a screw deck containing cortical screws of the indicated length having a 3.5 mm diameter. Further, a plate labeled "4.5 locking" contains locking screws of the indicated length and of a 4.5 mm diameter. The additional label plates 230, 232 and 234 supported on cross-bar 220 are ones that are used to replace plates 216, 218 as the screws in a particular screw deck dictate.

During a surgical procedure, a surgeon repairing a broken bone or otherwise needing a surgical screw will open the lid 134 of the screw tray 10 by manually depressing on the release legs 126, 128 of latch 106. This causes the openings 126A, 128A in the release legs to align with the spaced-apart openings 122A, 122B in the release bracket 118 and with the spaced-apart openings 124A, 124B in the latch plate 112. The coil spring 116 biases the latch plate 112 away from the fixed plate 108, thereby removing the inwardly extending feet 112C, 112D of the latch plate 112 from their locked position above the lid 134 and right side 58 of the tray frame 22. The lid 134 is now opened with the lid sleeves 162A, 164A of the lid brackets 162, 164 pivoting on the cantilever pins 102B, 104B of the respective lid brackets 102, 104 secured to the left depending rim 76 of the right frame wall 58 of the main frame 22.

With the lid 134 opened, the various surgical screws 244 are now in view. The surgeon can readily determine which screw to use by looking at the labels on plates 216, 218 which indicate the type and diameter of a screw, for example 3.5 locking. The removable inserts 246 indicate the screw length. After selecting a screw, a surgeon will verify its length by inserting the screw into inlet 236. The distal end of the screw will align with a length indicia 238, thereby verify the length. The surgeon will also insert the screw into the appropriate opening 240A to 240B, thereby verifying the screw diameter.

Figure 24:
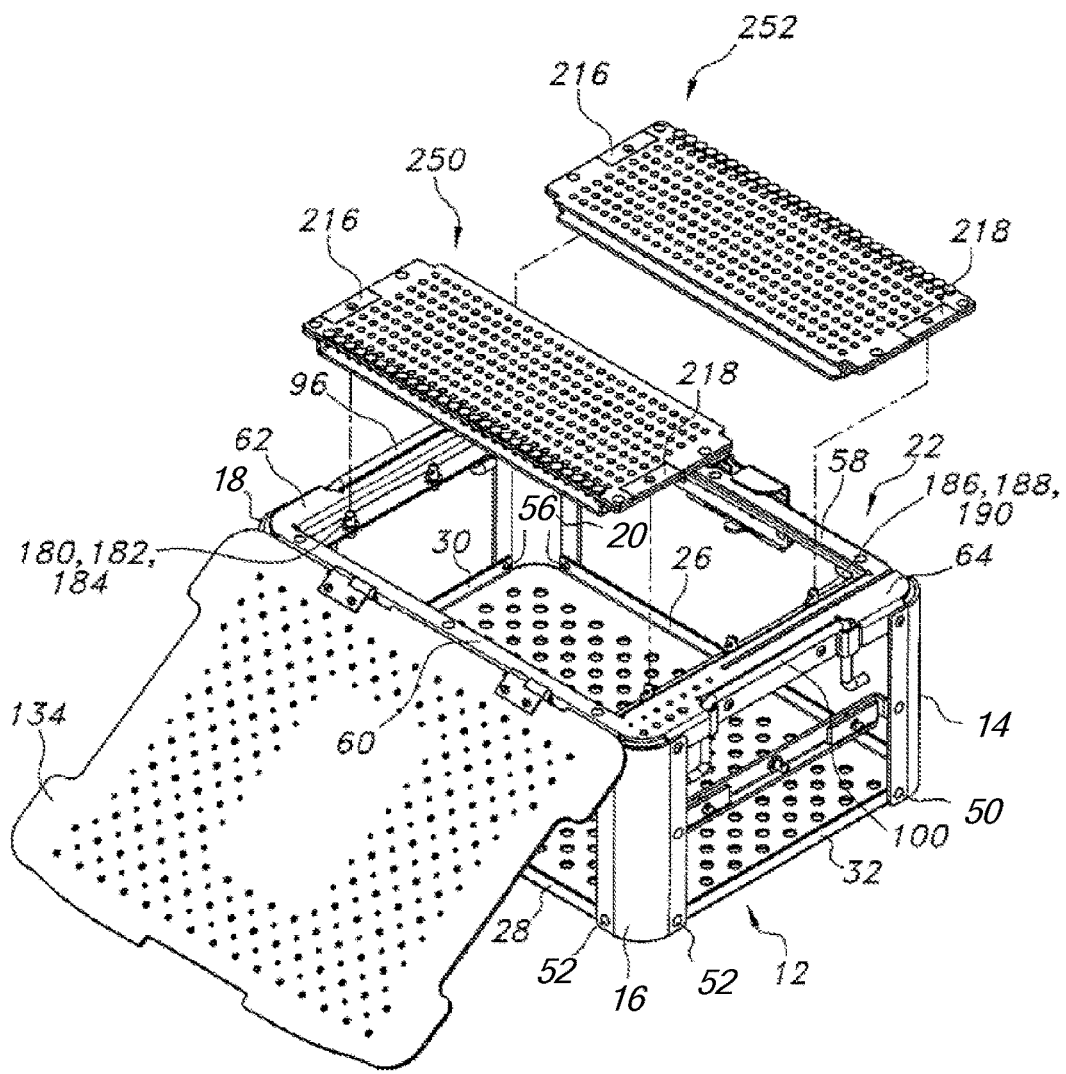
FIG. 24 is a perspective view of the screw tray 10 shown in FIG. 1, but with two single screw decks 250 and 252 occupying the area of the tray frame 22 shown occupied by screw decks 192, 210 and 212 in FIGS. 8, 9, 13 and 15.

Moreover, the various screw decks 192, 210 and 212 can be removed from the screw tray 10 by manipulation of the apposed spring-loaded catches 214 so that the decks can be separately cleaned and sterilized or replaced with a screw deck of a different size. FIG. 23 shows a single screw deck 248 that occupies the area of the tray frame 22 previously occupied by screw decks 192, 210 and 212. FIG. 24 shows an alternate embodiment where two screw decks 250 and 252 are sized to occupy the area of the tray frame 22.

Another embodiment of the present invention has the upper plate 194 of the exemplary screw deck 192 is provided with a column of first openings 202 running along the side 194C and a pattern of second openings 204 arranged in rows and columns throughout the remainder of the plate. However, the central planar portion 196A (FIG. 2) of the lower deck plate 196 does not have a column of first openings 206 adjacent to one of its major sides. That is because the removable inserts 246 are of a short enough length that they do not touch or contact the lower deck plate. Otherwise, in this alternate embodiment there are second openings 208 arranged in rows and columns throughout the lower deck plate with the pattern of columns and rows of second openings 204 in the upper plate 194 being aligned one above the other with the second openings 208 in the lower plate 196.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A system for holding and organizing at least two screws, the system comprising:
a) a screw deck, comprising:
i) a substantially planar upper deck plate extending along a longitudinal axis to spaced-apart right and left upper plate sides meeting opposed first and second upper plate ends, wherein the upper deck plate has a plurality of spaced apart first openings and a plurality of spaced apart second openings;
ii) a lower deck plate comprising spaced-apart right and left lower plate sides meeting opposed first and second lower plate ends, the lower deck plate comprising a substantially planar central lower plate portion meeting upwardly extending webs joined to first and second planar lower plate lips to thereby provide an elongated U-shape in cross-section extending along the longitudinal axis, wherein the first and second lower plate lips are secured to the upper deck plate ends so that the central lower plate portion is spaced from the upper deck plate, and wherein the lower deck plate has a plurality of spaced apart third openings, the second openings in the upper deck plate being aligned directly above the third openings in the lower deck plate;
b) at least one screw that is sized to be removably received in the plurality of second openings in the upper deck plate; and
c) at least one insert that is sized to removably fit into the plurality of first openings in the upper deck plate, wherein the insert is provided with a first label that correlates to a first characteristic of the at least one screw;
wherein the opposed first and second upper plate ends are provided with respective inlets that are spaced inwardly from the right and left upper plate sides;
wherein inlet plates are sized to fit into the inlets in the opposed first and second upper plate ends; and
wherein the inlet plates are provided with a second label corresponding to a second characteristic of the at least one screw.

2. The system of claim 1 wherein:
a) the first openings in the upper deck plate are arranged in a first column extending parallel to the longitudinal axis and adjacent to one of the right and left upper plate sides; and
b) the second openings in the upper deck plate are arranged in a second column extending parallel to the longitudinal axis, the first and second openings in the upper deck plate being aligned one immediately adjacent to the other; and
c) the third openings in the lower deck plate are arranged in a third column aligned directly below the second openings in the second column.

3. The system of claim 1 wherein the plurality of second and third openings in the respective upper and lower deck plates are arranged in at least two columns, each column having from 2 to 30 openings.

4. The system of claim 1 wherein the plurality of second and third openings in the respective upper and lower deck plates are arranged in from two to seven columns, each column having from 2 to 30 openings.

5. The system of claim 1 wherein the plurality of first and second openings in the upper deck plate are of the same or different size.

6. The system of claim 1 wherein the first label on the removable insert correlates to a length of the at least one screw.

7. The-system of claim 1 wherein the second label on the inlet plates correlates to at least one of a diameter and a type of the at least one screw.

8. The system of claim 1 wherein the opposed first and second lower plate lips at the opposed first and second lower plate ends are provided with lip openings that are aligned with the respective inlets in the opposed first and second upper plate ends.

9. The system of claim 1 wherein there is a plurality of inserts, each insert being sized to removably fit into one of the plurality of first openings in the upper deck plate, and wherein at least two of the inserts have a different first label.

10. The system of claim 1 wherein there are a plurality of screws, each screw being sized to be removably received in one of the plurality of second openings in the upper deck plate.

11. The system of claim 10 wherein at least one of the screws is sized to be removably received in one of the plurality of aligned second and third openings in the respective upper deck plate and the lower deck plate.

12. The system of claim 1 wherein the at least one screw is a surgical screw.

13. The system of claim 1 comprising:
a) a plurality of inserts, each insert being sized to removably fit into one of the plurality of first openings in the upper deck plate, wherein at least two of the inserts have a different first label; and
b) a plurality of screws, each screw being sized to be removably received in one of the plurality of second openings aligned above the third openings in the respective upper and lower deck plates,
c) wherein the first label on one of the removable inserts correlates to a first characteristic of one of the screws.

14. A system for holding and organizing at least two screws, the system comprising:
a) a screw deck, comprising:
i) a substantially planar upper deck plate extending along a longitudinal axis to spaced-apart right and left upper plate sides meeting opposed first and second upper plate ends, wherein the upper deck plate has a plurality of spaced apart first openings and a plurality of spaced apart second openings;
ii) a lower deck plate comprising spaced-apart right and left lower plate sides meeting opposed first and second lower plate ends, the lower deck plate comprising a substantially planar central lower plate portion meeting upwardly extending webs joined to first and second planar lower plate lips to thereby provide an elongated U-shape in cross-section extending along the longitudinal axis, wherein the first and second lower plate lips are secured to the upper deck plate ends so that the central lower plate portion is spaced from the upper deck plate, and wherein the lower deck plate has a plurality of spaced apart third openings, the second openings in the upper deck plate being aligned directly above the third openings in the lower deck plate;
b) at least one screw that is sized to be removably received in the plurality of second openings in the upper deck plate; and
c) at least one insert that is sized to removably fit into the plurality of first openings in the upper deck plate, wherein the insert is provided with a first label that correlates to a first characteristic of the at least one screw;
wherein the opposed first and second upper plate ends are provided with respective inlets that are spaced inwardly from the right and left upper plate sides; and
wherein the opposed first and second lower plate lips at the opposed first and second lower plate ends are provided with lip openings that are aligned with the respective inlets in the opposed first and second upper plate ends.

15. The system of claim 1 wherein:
a) the first openings in the upper deck plate are arranged in a first column extending parallel to the longitudinal axis and adjacent to one of the right and left upper plate sides; and
b) the second openings in the upper deck plate are arranged in a second column extending parallel to the longitudinal axis, the first and second openings in the upper deck plate being aligned one immediately adjacent to the other; and
c) the third openings in the lower deck plate are arranged in a third column aligned directly below the second openings in the second column.

16. The system of claim 14 wherein the plurality of second and third openings in the respective upper and lower deck plates are arranged in at least two columns, each column having from 2 to 30 openings.

17. The system of claim 14 wherein the plurality of second and third openings in the respective upper and lower deck plates are arranged in from two to seven columns, each column having from 2 to 30 openings.

18. The system of claim 14 wherein the plurality of first and second openings in the upper deck plate are of the same or different size.

19. The system of claim 14 wherein the first label on the removable insert correlates to a length of the at least one screw.

20. The system of claim 14 comprising inlet plates that are sized to fit into the inlets in the opposed first and second upper plate ends.

21. The system of claim 20 wherein the inlet plates are provided with a second label corresponding to a second characteristic of the at least one screw.

22. The system of claim 21 wherein the second label on the inlet plates correlates to at least one of a diameter and a type of the at least one screw.

23. The system of claim 14 wherein there is a plurality of inserts, each insert being sized to removably fit into one of the plurality of first openings in the upper deck plate, and wherein at least two of the inserts have a different first label.

24. The system of claim 14 wherein there are a plurality of screws, each screw being sized to be removably received in one of the plurality of second openings in the upper deck plate.

25. The system of claim 24 wherein at least one of the screws is sized to be removably received in one of the plurality of aligned second and third openings in the respective upper deck plate and the lower deck plate.

26. The system of claim 14 wherein the at least one screw is a surgical screw.

27. The system of claim 14 comprising:
a) a plurality of inserts, each insert being sized to removably fit into one of the plurality of first openings in the upper deck plate, wherein at least two of the inserts have a different first label; and
b) a plurality of screws, each screw being sized to be removably received in one of the plurality of second openings aligned above the third openings in the respective upper and lower deck plates,
c) wherein the first label on one of the removable inserts correlates to a first characteristic of one of the screws.

* * * * *